United States Patent
He et al.

(10) Patent No.: US 7,205,328 B2
(45) Date of Patent: Apr. 17, 2007

(54) OXINDOLES WITH ANTI-HIV ACTIVITY

(75) Inventors: Yun He, San Diego, CA (US); Tao Jiang, San Diego, CA (US); Kelli L. Kuhen, Carlsbad, CA (US); David Archer Ellis, San Diego, CA (US); Baogen Wu, San Diego, CA (US); Tom Yao-Hsiang Wu, La Jolla, CA (US); Badry Bursulaya, San Diego, CA (US)

(73) Assignee: IRM LLC, Hamilton (BM)

( * ) Notice: Subject to any disclaimer, the term of this patent is extended or adjusted under 35 U.S.C. 154(b) by 387 days.

(21) Appl. No.: 10/690,802

(22) Filed: Oct. 21, 2003

(65) Prior Publication Data

US 2004/0152755 A1   Aug. 5, 2004

Related U.S. Application Data

(60) Provisional application No. 60/420,482, filed on Oct. 21, 2002, provisional application No. 60/420,481, filed on Oct. 21, 2002.

(51) Int. Cl.
*A61K 31/405* (2006.01)
*C07D 209/96* (2006.01)

(52) U.S. Cl. .............. 514/409; 514/269; 514/299; 514/399; 544/298; 546/277.1; 548/411

(58) Field of Classification Search ............ 548/408, 548/409, 410; 514/409
See application file for complete search history.

(56) References Cited

U.S. PATENT DOCUMENTS 6,391,907 B1 * 5/2002 Fensome et al. ............ 514/409
6,608,068 B2 * 8/2003 Fensome et al. ............ 514/256

FOREIGN PATENT DOCUMENTS

JP        57-102863 A    6/1982
WO   WO 2001/077100 A2  10/2001

OTHER PUBLICATIONS

Database CAPLUS on STN, (Columbus, OH, USA), 126:185970, MOLDVAI, 'Chemistry of indoles carrying a basic function. Part 3. Synthesis of spiro(cyclopropane-1, 3'[3H]indol}-2'(1H)-ones with antihypoxic effects', abstract, Archiv der Pharmazie, (1996), vol. 329, No. 12, pp. 541-549. See, for example, the compound of CA Registry No. 187325-59-3.

Database CAPLUS on STN, (Columbus, OH, USA) 89:108935, Frank, 'Spirocyclic 2-indolinones by 1,3-dipolar cycloaddition', abstract, Justis Liebigs Annalen der Chemie (1978), vol. 5, pp. 717-725. See, for example, the compound of CA Registry No. 67503-06-4.

* cited by examiner

*Primary Examiner*—Kamal A. Saeed
(74) *Attorney, Agent, or Firm*—Emily Tongro Wu; Genomics Institute of the Novartis Research Foundation

(57) ABSTRACT

The present invention relates to inhibition of viruses, e.g., HIV using oxindoles and compounds related to oxindoles. The invention further relates to methods for identifying and using agents, including small molecule chemical compositions that inhibit HIV in a cell; as well as to methods of prophylaxis, and therapy related to HIV infection and related disease states such as AIDS.

24 Claims, 21 Drawing Sheets

FIG. 1A

| Compound Number | Structure | Physical Data<br>¹H NMR 400 MHz (DMSO-$d_6$) and/or MS (m/z) |
|---|---|---|
| 1 | (5-bromo spirooxindole cyclopropane ethyl ester) | ¹H NMR (CCl3D): δ 7.89 (br, 1H), 7.52 (br, 1H), 7.35 (m, 1H), 6.82 (m, 1H), 4.12 (t, 2H), 2.72 (m, 1H), 2.16 (m, 1H), 2.04 (m, 1H), 1.25 (m, 3H). MS: m/z 310 [M+1]+. |
| 2 | (5-fluoro spirooxindole cyclopropane isopropyl ester) | ¹H NMR (500 *MHz*, CDCl₃) δ 7.73 (s, 1H), 4.16 (dd, J = 2.6 Hz, 9.2 Hz, 1H), 6.93 (dt, J = 2.6 Hz, 8.6 Hz, 1H), 6.84 (dd, J = 4.4 Hz, 8.6 Hz, 1H), 4.98-5.07 (m, 1H), 2.69 (t, J = 8.1 Hz, 1H), 2.12 (dd, J = 4.4 Hz, 7.3 Hz, 1H), 2.02 (dd, J = 4.4 Hz, 8.8 Hz, 1H), 1.26 (d, J = 6.2 Hz, 3H), 1.12 (d, J = 6.2 Hz, 3H). MS *m/z* 264.1 (M + 1). |
| 3 | (5-bromo spirooxindole cyclopropane isopropyl ester) | ¹H NMR (500 *MHz*, CDCl₃) δ 8.05 (br, 1H), 7.51 (s, 1H), 7.34 (d, J = 8.2 Hz, 1H), 6.81 (d, J = 8.2 Hz, 1H), 5.00-5.08 (m, 2H), 2.69 (t, J = 8.2 Hz, 1H), 2.14 (dd, J = 4.7 Hz, 7.6 Hz, 1H), 2.02 (dd, J = 4.4 Hz, 8.5 Hz, 1H), 1.58 (s, 1H), 1.27 (d, J = 6.2 Hz, 3H), 1.14 (J = 6.2 Hz, 3H). MS *m/z* 324 (M + 1). |
| 4 | (5-cyano spirooxindole cyclopropane ethyl ester) | MS *m/z* 257.2 (M + 1). |
| 5 | (spirooxindole cyclopropane ethyl ester) | ¹H NMR (500 *MHz*, CDCl₃) δ 9.00 (s, 1H), 7.34 (d, J = 7.7 Hz, 1H), 7.23 (t, J = 7.8 Hz, 1H), 6.96-7.02 (m, 2H), 4.07-4.22 (m, 2H), 2.72 (d, J = 7.3 Hz, 1H), 2.16 (dd, J = 4.4 Hz, 7.3 Hz, 1H), 2.03 (dd, J = 4.4 Hz, 8.8 Hz, 1H), 1.21 (t, J = 7.3 Hz, 3H). MS *m/z* 232.1 (M + 1). |

FIG. 1B

| Compound Number | Structure | Physical Data<br>¹H NMR 400 MHz (DMSO-$d_6$) and/or MS (m/z) |
|---|---|---|
| 6 | (5-bromo-2-oxoindoline-spirocyclopropane with N-methoxy-N-methyl carboxamide) | MS m/z 325.0 (M + 1). |
| 7 | (5-chloro-2-oxoindoline-spirocyclopropane ethyl ester) | MS m/z 266.1 (M + 1). |
| 8 | (5-chloro-7-methyl-2-oxoindoline-spirocyclopropane ethyl ester) | MS m/z 280.1 (M + 1). |
| 9 | (5-nitro-2-oxoindoline-spirocyclopropane ethyl ester) | MS m/z 277.1 (M + 1). |
| 10 | (5-iodo-2-oxoindoline-spirocyclopropane ethyl ester) | MS m/z 358.0 (M + 1). |

FIG. 1C

| Compound Number | Structure | Physical Data<br>$^1$H NMR 400 MHz (DMSO-$d_6$) and/or MS (m/z) |
|---|---|---|
| 11 | (F$_3$CO-substituted spiro[cyclopropane-1,3'-indolin]-2'-one with ethyl ester) | MS m/z 316.1 (M + 1). |
| 12 | (5-Br spiro[cyclopropane-1,3'-indolin]-2'-one with tert-butyl ester) | MS m/z 338.1 (M + 1). |
| 13 | (5-Br spiro[cyclopropane-1,3'-indolin]-2'-one with benzyl ester) | MS m/z 372.0 (M + 1). |
| 14 | (5-Br spiro[cyclopropane-1,3'-indolin]-2'-one with pentanoyl group) | MS m/z 322.0 (M + 1). |
| 15 | (5,6-diCl spiro[cyclopropane-1,3'-indolin]-2'-one with ethyl ester) | MS m/z 300.0 (M + 1). |

FIG. 1D

| Compound Number | Structure | Physical Data $^1$H NMR 400 MHz (DMSO-$d_6$) and/or MS (m/z) |
|---|---|---|
| 16 | (5-phenyl spiro[indoline-3,1'-cyclopropane]-2-one with ethyl ester) | MS m/z 308.2 (M + 1). |
| 17 | (5-(1-methylpyrrol-2-yl) spiro[indoline-3,1'-cyclopropane]-2-one with ethyl ester) | MS m/z 311.2 (M + 1). |
| 18 | (5-(furan-2-yl) spiro[indoline-3,1'-cyclopropane]-2-one with ethyl ester) | MS m/z 298.2 (M + 1). |
| 19 | (5-(thiophen-2-yl) spiro[indoline-3,1'-cyclopropane]-2-one with ethyl ester) | MS m/z 314.1 (M + 1). |
| 20 | (5-vinyl spiro[indoline-3,1'-cyclopropane]-2-one with ethyl ester) | MS m/z 258.1 (M + 1). |

| Compound Number | Structure | Physical Data $^1$H NMR 400 MHz (DMSO-$d_6$) and/or MS (m/z) |
|---|---|---|
| 21 | 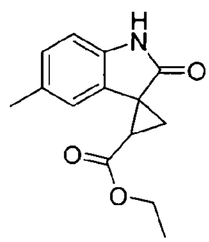 | MS m/z 246.1 (M + 1). |
| 22 | 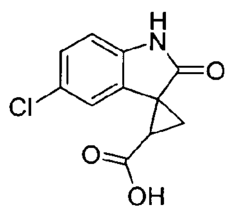 | MS m/z 238.1 (M + 1). |
| 23 | 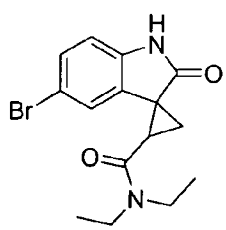 | MS: m/z 337 [M+1]+. |
| 24 | 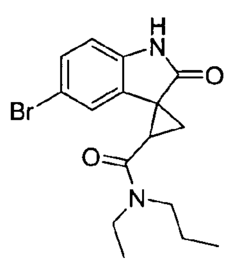 | MS m/z 352.1 (M + 1). |
| 25 | 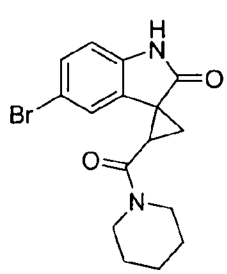 | MS m/z 349.1 (M + 1). |

| Compound Number | Structure | Physical Data $^1$H NMR 400 MHz (DMSO-$d_6$) and/or MS (m/z) |
|---|---|---|
| 26 | 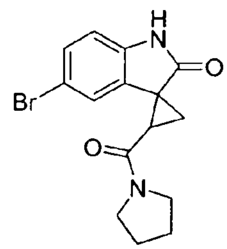 | MS m/z 335.0 (M + 1). |
| 27 | 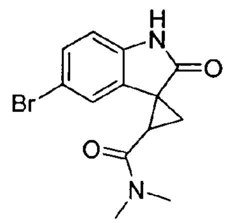 | MS m/z 309.0 (M + 1). |
| 28 | 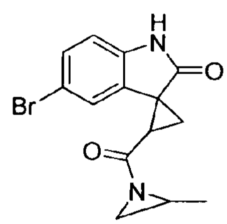 | MS m/z 321.0 (M + 1). |
| 29 | 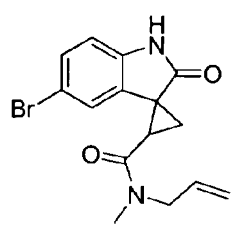 | MS m/z 335.0 (M + 1). |
| 30 | 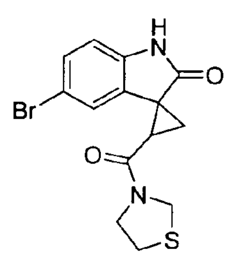 | MS m/z 353.0 (M + 1). |

FIG. 1G

| Compound Number | Structure | Physical Data<br>¹H NMR 400 MHz (DMSO-$d_6$) and/or MS (m/z) |
|---|---|---|
| 31 | 5-bromo spirooxindole cyclopropane with N-methyl-N-(2-cyanoethyl)carboxamide | MS m/z 348.0 (M + 1). |
| 32 | 5-bromo spirooxindole cyclopropane with N-methyl-N-ethylcarboxamide | MS m/z 323.0 (M + 1). |
| 33 | 5-chloro spirooxindole cyclopropane with 2-pyridyl | ¹H NMR (DMSO-d6): δ 8.76 (s, 1H), 8.64 (m, 1H), 7.62 (m, 1H), 7.25 (m, 1H), 7.20 (m, 1H), 7.05 (m, 1H), 6.82 (d, 1H), 6.79(d, 1H), 3.36 (t, 1H), 2.65 (m, 1H), 2.25 (m, 1H). MS: m/z 271 [M+1]+. |
| 34 | 5-bromo spirooxindole cyclopropane with N-methyltetrazole | ¹H NMR (CDCl3): δ 8.52 (s, 1H), 7.27 (m, 1H), 7.04 (br, 1H), 6.80 (m, 1H), 4.34 (s, 3H), 3.35 (t, 1H), 2.48 (m, 1H), 2.05 (m, 1H). MS m/z 320 [M+1]+. |

FIG. 1H

| Compound Number | Structure | Physical Data<br>¹H NMR 400 MHz (DMSO-$d_6$) and/or MS (m/z) |
|---|---|---|
| 35 | (5-chloro-indolin-2-one spiro-cyclopropane with 5-methylfuran-2-yl) | MS m/z 273.9 (M + 1). |
| 36 | (5-chloro-indolin-2-one spiro-cyclopropane with 5-bromofuran-2-yl) | MS m/z 337.8 (M + 1). |
| 37 | (5-chloro-indolin-2-one spiro-cyclopropane with benzofuran-2-yl) | MS m/z 309.9 (M + 1). |
| 38 | (5-chloro-indolin-2-one spiro-cyclopropane with thiophen-3-yl) | MS m/z 275.9 (M + 1). |
| 39 | (5-chloro-indolin-2-one spiro-cyclopropane with 5-ethylthiophen-2-yl) | MS m/z 304.1 (M + 1). |

| Compound Number | Structure | Physical Data<br>$^1$H NMR 400 MHz (DMSO-$d_6$) and/or MS (m/z) |
|---|---|---|
| 40 | 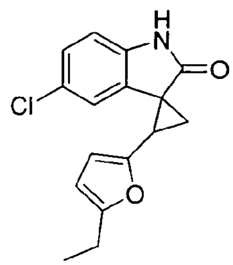 | MS m/z 288.1 (M + 1). |
| 41 | 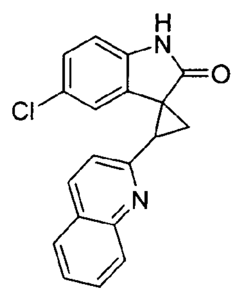 | MS m/z 321.1 (M + 1). |
| 42 | 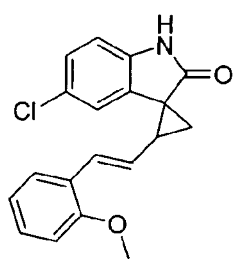 | MS m/z 326.1 (M + 1). |
| 43 | 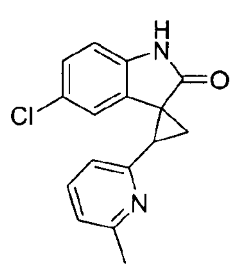 | MS m/z 285.1 (M + 1). |

FIG. 1J

| Compound Number | Structure | Physical Data<br>¹H NMR 400 MHz (DMSO-$d_6$) and/or MS (m/z) |
|---|---|---|
| 44 | 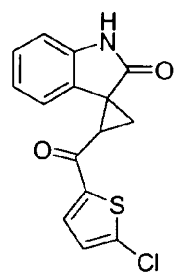 | MS m/z 304.0 (M + 1). |
| 45 | 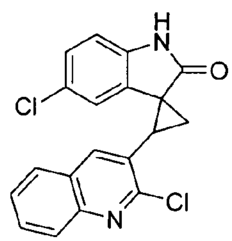 | MS m/z 355.0 (M + 1). |
| 46 | 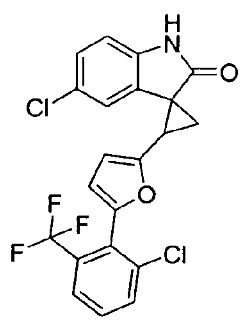 | MS m/z 438.3 (M + 1). |
| 47 | 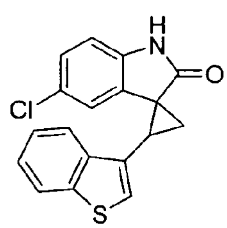 | MS m/z 326.3 (M + 1). |

| Compound Number | Structure | Physical Data<br>¹H NMR 400 MHz (DMSO-$d_6$) and/or MS (m/z) |
|---|---|---|
| 48 | 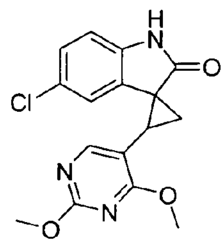 | MS m/z 332.3 (M + 1). |
| 49 | 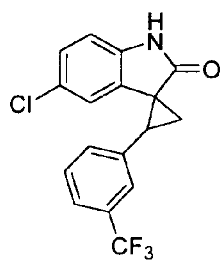 | MS m/z 338.4 (M + 1). |
| 50 | 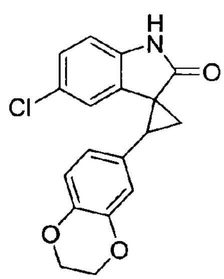 | MS m/z 328.4 (M + 1). |
| 51 | 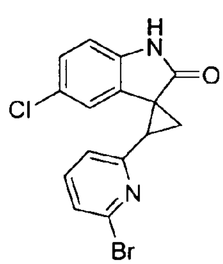 | MS m/z 351.3 (M + 1). |

| Compound Number | Structure | Physical Data $^1$H NMR 400 MHz (DMSO-$d_6$) and/or MS (m/z) |
|---|---|---|
| 52 | 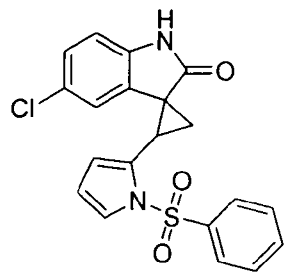 | MS m/z 399.3 (M + 1). |
| 53 | 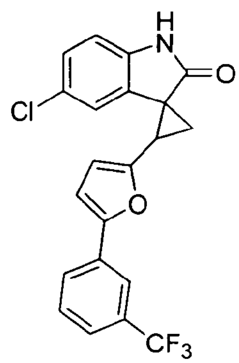 | MS m/z 404.3 (M + 1). |
| 54 | 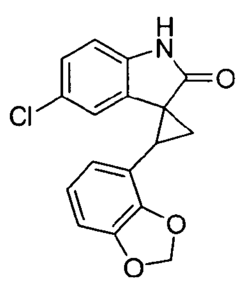 | MS m/z 314.4 (M + 1). |
| 55 | 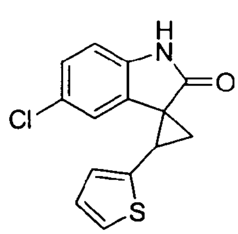 | MS m/z 276.1 (M + 1). |

FIG. 1M

| Compound Number | Structure | Physical Data $^1$H NMR 400 MHz (DMSO-$d_6$) and/or MS (m/z) |
|---|---|---|
| 56 | 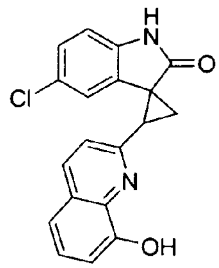 | MS m/z 337.1 (M + 1). |
| 57 | 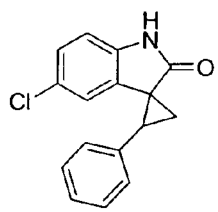 | $^1$H NMR (DMSO-d$_6$): δ 8.01 (s, 1H), 7.28 (m, 3H), 7.18 (m, 2H), 7.05 (m, 1H), 6.82 (d, 1H), 5.88 (d, 1H), 3.38 (t, 1H), 2.24 (m, 1H), 2.03 (m, 1H) ; MS m/z 270.3 (M + 1). |
| 58 | 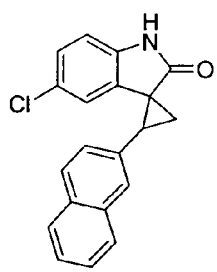 | $^1$H NMR (DMSO-d$_6$): δ 8.58 (s, 1H), 7.81 (m, 2H), 7.75 (m, 2H), 7.48(m, 2H), 7.19(d, 1H), 7.03 (d, 1H), 6.85 (d, 1H), 5.94 (s, 1H), 3.55 (t, 1H), 2.33 (m, 1H), 2.05 (m, 1H) ; MS m/z 270.3 (M + 1). |
| 59 | 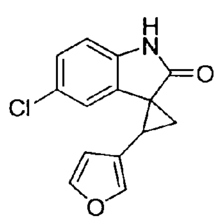 | MS m/z 260.3 (M + 1). |
| 60 | 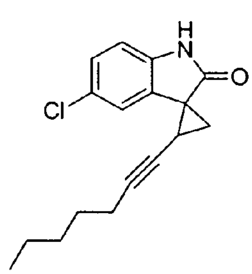 | MS m/z 288.3 (M + 1). |

| Compound Number | Structure | Physical Data<br>$^1$H NMR 400 MHz (DMSO-$d_6$) and/or MS (m/z) |
|---|---|---|
| 61 | 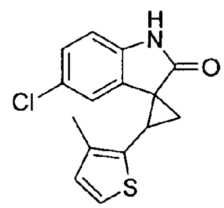 | MS m/z 290.3 (M + 1). |
| 62 | 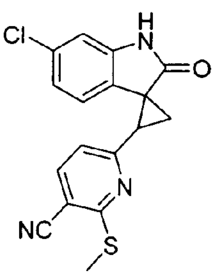 | MS m/z 342.3 (M + 1). |
| 63 | 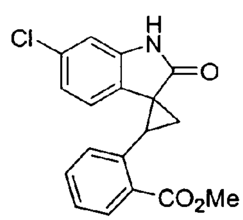 | MS m/z 328.3 (M + 1). |
| 64 | 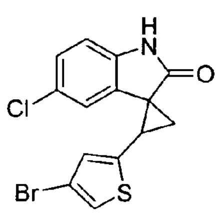 | MS m/z 354.2 (M + 1). |
| 65 | 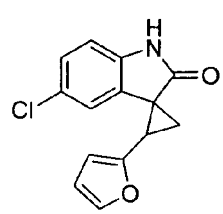 | MS m/z 260.3 (M + 1). |

FIG. 10

| Compound Number | Structure | Physical Data<br>¹H NMR 400 MHz (DMSO-$d_6$) and/or MS (m/z) |
|---|---|---|
| 66 | (6-chloro spirooxindole-cyclopropane with pyridine-CH=CH-C(O)CH₃) | MS m/z 339.3 (M + 1). |
| 67 | (5-chloro spirooxindole-cyclopropane with 4-bromothiophene) | MS m/z 354.2 (M + 1). |
| 68 | (5-chloro spirooxindole-cyclopropane with quinoline) | MS m/z 321.3 (M + 1). |
| 69 | (5-chloro spirooxindole-cyclopropane with methoxy-dimethylpyridine) | ¹H NMR (DMSO-$d_6$): δ 10.61 (s, 1H), 8.16 (s, 1H), 6.93 (d, 1H), 6.68 (d, 1H), 5.71 (d, 1H), 3.42 (s, 3H), 2.95 (t, 1H), 2.36 (m, 1H), 2.04 (s, 3H), 1.84 (m, 1H), 1.60 (s, 3H); MS m/z 329.4 (M + 1). |
| 70 | (5-chloro spirooxindole-cyclopropane with nitro-dimethylpyridine) | ¹H NMR (CDCl₃-d): δ 8.56 (s, 1H), 7.59 (br, 1H), 7.12 (d, 1H), 6.84 (d, 1H), 6.38 (d, 1H), 3.52 (t, 1H), 2.76 (m, 1H), 2.32 (m, 4H), 2.02 (s, 3H); MS m/z 344.3 (M + 1). |

FIG. 1P

| Compound Number | Structure | Physical Data<br>¹H NMR 400 MHz (DMSO-$d_6$) and/or MS (m/z) |
|---|---|---|
| 71 | (structure: 5-chloro-spirooxindole-cyclopropane with 5-bromopyridin-2-yl) | ¹H NMR (DMSO-$d_6$): δ 10.08 (s, 1H), 8.75 (d, 1H), 8.00 (m, 1H), 7.51(d, 1H), 7.12(m, 1H), 6.86 (d, 1H), 6.72 (d, 1H), 3.19 (t, 1H), 2.56 (m, 1H), 2.04 (m, 1H); MS m/z 349.2 (M + 1). |
| 72 | (structure: 5-chloro-spirooxindole-cyclopropane with 6-phenylpyridin-2-yl) | 1H NMR (CDCl3): δ 8.28 (m, 2H), 8.06 (s, 1H), 7.64 (m, 2H), 7.51 (m, 2H), 7.40 (m, 1H), 7.18 (m, 1H), 7.02 (m, 2H), 6.75 (d, 1H), 3.48 (1H), 2.86 (m, 1H), 2.29 (m, 1H). MS: m/z 347 [M+1]+. |
| 73 | (structure: 5-chloro-spirooxindole-cyclopropane with 6-vinylpyridin-2-yl) | ¹H NMR (CDCl₃-d): δ 7.85 (s, 1H), 7.51(t, 1H), 7.23 (d, 1H), 7.11 (d, 1H), 7.09 (d, 1H), 7.04 (m, 1H), 6.81(t, 1H), 6.74 (d, 1H), 6.15 (d, 1H), 5.46(d, 1H), 3.25 (t, 1H), 2.63 (m, 1H), 2.23 (m, 1H) ; MS m/z 297.3 (M + 1). |
| 74 | (structure: 5-chloro-spirooxindole-cyclopropane with 6-(furan-2-yl)pyridin-2-yl) | MS m/z 337.3 (M + 1). |

FIG. 1Q

| Compound Number | Structure | Physical Data $^1$H NMR 400 MHz (DMSO-$d_6$) and/or MS (m/z) |
|---|---|---|
| 75 | 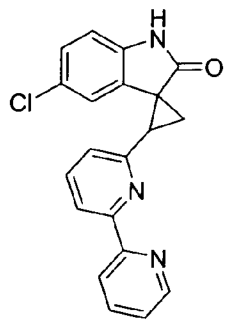 | $^1$H NMR (CDCl$_3$-d): δ 8.92 (d, 1H), 8.74 (d, 1H), 8.54 (d, 1H), 8.16 (s, 1H), 8.10 (m, 1H), 7.94 (t, 1H), 7.56 (m, 1H), 7.47 (m, 2H), 7.22 (m, 1H), 6.97 (d, 1H), 3.59 (t, 1H), 3.05 (m, 1H), 2.53 (m, 1H); MS m/z 348.3 (M + 1). |
| 76 | 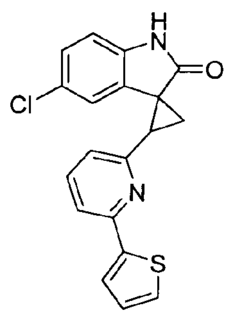 | $^1$H NMR (CDCl$_3$-d): δ 7.83 (d, 1H), 7.70-7.82 (m, 3H), 7.65 (d, 1H), 7.51 (br, 1H), 7.36 (t, 1H), 7.30 (d, 1H), 7.23 (dd, 1H), 6.95 (d, 1H), 3.48 (t, 1H), 3.05 (m, 1H), 2.49 (m, 1H); MS m/z 353.3 (M + 1). |
| 77 | 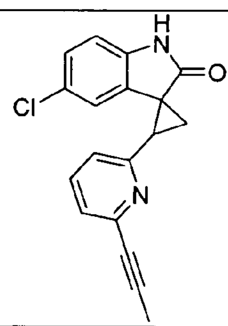 | $^1$H NMR (CDCl$_3$-d): δ 7.85 (s, 1H), 7.51(t, 1H), 7.23 (d, 1H), 7.11 (d, 1H), 7.09 (d, 1H), 7.04 (m, 1H), 6.74 (d, 1H), 3.25 (t, 1H), 2.64 (m, 1H), 2.23 (m, 1H), 2.11 (s, 3H); MS m/z 309.3 (M + 1). |
| 78 | 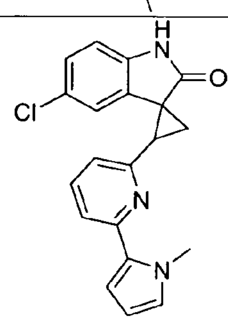 | $^1$H NMR (CDCl$_3$-d): δ 7.50 (s, 1H), 7.48 (t, 1H), 7.36 (d, 1H), 6.95 (m, 2H), 6.70 (m, 2H), 6.53 (m, 2H), 6.13 (m, 1H), 3.89 (s, 3H), 3.31 (t, 1H), 2.52 (m, 1H), 2.19 (m, 1H); MS m/z 350.3 (M + 1). |

| Compound Number | Structure | Physical Data<br>¹H NMR 400 MHz (DMSO-$d_6$) and/or MS (m/z) |
|---|---|---|
| 79 | 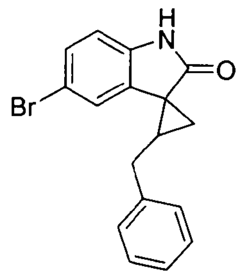 | ¹H NMR (CDCl₃-d): δ 8.29 (s, 1H), 7.36 (dd, 1H), 7.28 (m, 2H), 7.21 (m, 3H), 7.14 (d, 1H), 6.87 (d, 1H), 3.00 (d, 2H), 2.27 (m, 1H), 2.11 (m, 1H), 1.48 (m, 1H); MS m/z 328.3 (M + 1). |
| 80 | 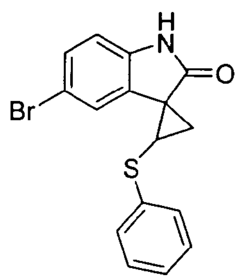 | ¹H NMR (CDCl₃-d): δ 7.72 (s, 1H), 7.37 (m, 1H), 7.09-7.23 (m, 5H), 7.03 (d, 1H), 6.85 (d, 1H), 3.22 (t, 1H), 2.15-2.25 (m, 2H), MS m/z 346.2 (M + 1). |
| 81 | 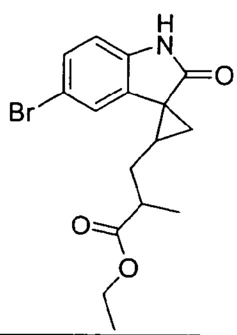 | ¹H NMR (CDCl₃-d): δ 8.24 (s, 1H), 7.42 (d, 1H), 7.09 (d, 1H), 6.78 (d, 1H), 4.08 (m, 2H), 2.46 (m, 1H), 2.04 (m, 3H), 1.81 (m, 1H), 1.41 (m, 1H), 1.18 (m, 6H); MS m/z 352.3 (M + 1). |
| 82 | 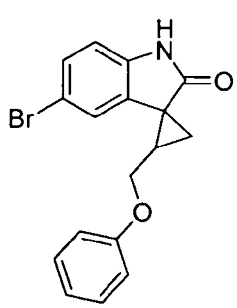 | ¹H NMR (CDCl₃-d): δ 7.62 (s, 1H), 7.26-7.37 (m, 4H), 7.12 (br, 1H), 6.97 (t, 1H), 6.88 (d, 1H), 6.81 (d, 1H), 4.24 (m, 2H), 2.46 (m, 1H), 2.03 (m, 1H), 1.69 (m, 1H); MS m/z 344.3 (M + 1). |

FIG. 1S

| Compound Number | Structure | Physical Data<br>¹H NMR 400 MHz (DMSO-$d_6$) and/or MS (m/z) |
|---|---|---|
| 83 | 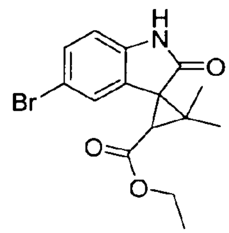 | ¹H NMR (500 MHz, CDCl3): δ 7.83 (br, 1H), 7.76 (s, 1H), 7.33 (d, J = 8.2 Hz, 1H), 6.78 (d, J = 8.2 Hz, 1H), 4.15 (t, J = 7.3 Hz, 2H), 2.78 (s, 1H), 1.57 (s, 3H), 1.56 (s, 3H), 1.26 (t, J = 7.3 Hz, 3H). MS: m/z 338 [M+1]+. |
| 84 | 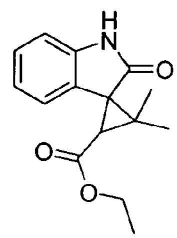 | ¹H NMR (500 *MHz*, CDCl$_3$) δ 7.60 (d, J = 7.7 Hz, 1H), 7.21 (t, J = 7.7 Hz, 1H), 7.02 (t, J = 7.7 Hz, 1H), 6.91 (d, J = 8.8 Hz, 1H), 4.08-4.18 (m, 2H), 2.79 (s, 1H), 1.59 (s, 3H), 1.58 (s, 3H), 1.24 (t, J = 7.3 Hz, 3H). MS *m/z* 260.1 (M + 1). |
| 85 | 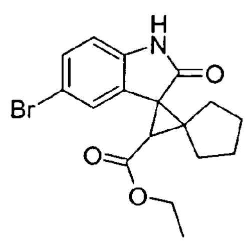 | ¹H NMR (500 MHz, CDCl3) δ 7.76 (s, 1H), 7.68 (s, 1H), 7.33 (d, J = 8.2 Hz, 1H), 6.78 (d, J = 8.2 Hz, 1H), 4.14-4.16 (m, 2H), 2.81 (s, 1H), 2.37-2.42 (m, 1H), 2.04-2.15 (m, 2H), 1.87-1.93 (m, 1H), 1.70-1.78 (m, 2H), 1.59-1.66 (m, 2H), 1.25 (t, J = 7.3 Hz, 3H). MS *m/z* 364.0 (M + 1). |
| 86 | 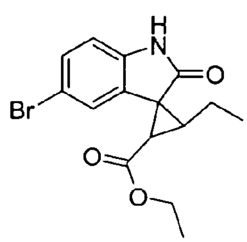 | MS *m/z* 338.0 (M + 1). |
| 87 | 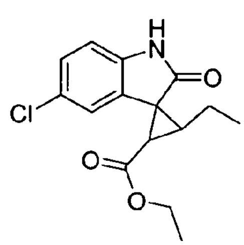 | MS *m/z* 294.1 (M + 1). |

| Compound Number | Structure | Physical Data $^1$H NMR 400 MHz (DMSO-$d_6$) and/or MS (m/z) |
|---|---|---|
| 88 | 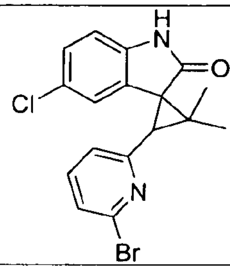 | $^1$H NMR (DMSO-$d_6$): δ 10.59 (s, 1H), 7.55 (m, 1H), 7.40 (d, 1H), 7.22 (d, 1H), 7.03(m, 1H), 6.70 (m, 2H), 3.01 (s, 1H), 1.42 (s, 3H), 1.24 (s, 3H); MS m/z 377.2 (M + 1). |
| 89 | 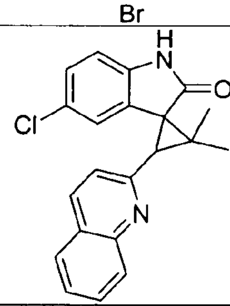 | $^1$H NMR (CDCl$_3$-d): δ 8.01 (m, 2H), 7.94 (br, 1H), 7.73 (m, 1H), 7.65 (m, 1H), 7.47 (m, 1H), 7.12 (d, 1H), 7.04(m, 1H), 6.90 (d, 1H), 6.74 (d, 1H), 3.48 (s, 1H), 1.50 (s, 3H), 1.46 (s, 3H); MS m/z 349.4 (M + 1). |
| 90 | 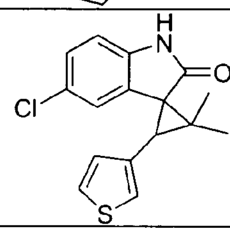 | $^1$H NMR (CDCl$_3$-d): δ 9.40 (s, 1H), 7.24 (m, 1H), 7.13-7.17 (m, 2H), 7.02 (d, 1H), 6.92 (dd, 1H), 6.67 (d, 1H), 3.00 (s, 1H), 1.56 (d, 6H); MS m/z 304.3 (M + 1). |
| 91 | 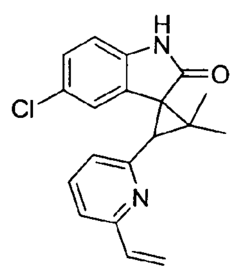 | $^1$H NMR (CDCl$_3$-d): δ 8.49 (s, 1H), 7.38(t, 1H), 7.21 (d, 1H), 7.09 (m, 1H), 6.93 (d, 1H), 6.81 (m, 2H), 6.71(d, 1H), 6.16 (d, 1H), 5.48(d, 1H), 3.40 (s, 1H), 1.70(s, 3H), 1.62 (s, 3H); MS m/z 325.3 (M + 1). |
| 92 | 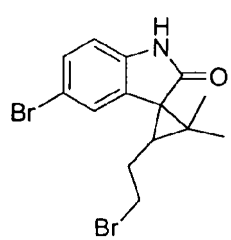 | MS m/z 374.2 (M + 1). |

| Compound Number | Structure | Physical Data<br>¹H NMR 400 MHz (DMSO-$d_6$) and/or MS (m/z) |
|---|---|---|
| 93 | 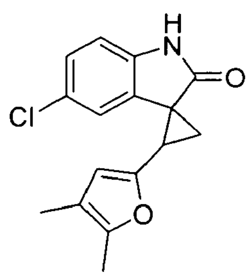 | MS *m/z* 288 (M + 1). |

OXINDOLES WITH ANTI-HIV ACTIVITY

CROSS-REFERENCE TO RELATED APPLICATIONS

This is a non-provisional filing of U.S. Provisional Patent Application No. 60/420,482 filed on Oct. 21, 2002, the disclosure of which is incorporated herein by reference in its entirety for all purposes.

FIELD OF THE INVENTION

The present invention relates to inhibition of a virus, e.g., HIV, using oxindole-based compounds. The compounds of the invention are of use to combat infection by mutant, drug-sensitive, drug-resistant, and multi-drug resistant strains of HIV. The invention further relates to methods for identifying and using to inhibit HIV and to treat HIV-related diseases.

BACKGROUND OF THE INVENTION

The Human Immunodeficiency Virus (HIV) infects millions of people globally. Cases are reported from nearly every country amounting to 40 million adults and children living with HIV/AIDS worldwide. In 2001, 5 million people were newly infected with HIV, and there were 3 million adult and child deaths due to HIV/AIDS. A full third of those people living with AIDS are aged 15–24. (World Health Organization, 2001). HIV/AIDS treatments exist, however, the drugs currently used in treatment modalities exhibit numerous side effects, require prolonged treatment that often induces drug resistance, and do not result in complete eradication of the virus from the body.

The disease AIDS is the end result of an HIV-1 or HIV-2 virus following its own complex life cycle. The virion life cycle begins with the virion attaching itself to the host human T-4 lymphocyte immune cell through the bonding of a glycoprotein on the surface of the virion's protective coat with the CD4 glycoprotein on the lymphocyte cell. Once attached, the virion sheds its glycoprotein coat, penetrates into the membrane of the host cell, and uncoats its RNA. The virion enzyme, reverse transcriptase, directs the process of transcribing the RNA into single-stranded DNA. The viral RNA is degraded and a second DNA strand is created. The now double-stranded DNA is integrated into the human cell's genes and those genes are used for virus reproduction.

At this point, RNA polymerase transcribes the integrated DNA into viral RNA. The viral RNA is translated into the precursor gag-pol fusion polyprotein. The polyprotein is then cleaved by the HIV protease to yield the mature viral proteins. Thus, HIV protease is responsible for regulating a cascade of cleavage events that lead to the virus particle's maturing into a virus that is capable of full infectivity.

The typical human immune system response, killing the invading virion, is taxed because the virus infects and kills the immune system's T cells. In addition, viral reverse transcriptase, the enzyme used in making a new virion particle, is not very specific, and causes transcription mistakes that result in continually changed glycoproteins on the surface of the viral protective coat. This lack of specificity decreases the immune system's effectiveness because antibodies specifically produced against one glycoprotein may be useless against another, hence reducing the number of antibodies available to fight the virus. The virus continues to reproduce while the immune response system continues to weaken. Eventually, the HIV largely holds free reign over the body's immune system, allowing opportunistic infections to set in and, without the administration of antiviral agents, immunomodulators, or both, death may result.

There are at least three critical points in the virus's life cycle which have been identified as possible targets for antiviral drugs: (1) the initial attachment of the virion to the T-4 lymphocyte or macrophage site; (2) the transcription of viral RNA to viral DNA (reverse transcriptase, RT); and (3) the processing of gag-pol protein by HIV protease.

Inhibition of the virus at the second critical point, the viral RNA to viral DNA transcription process, has provided a number of the current therapies used in treading AIDS. This transcription must occur for the virion to reproduce because the virion's genes are encoded in RNA and the host cell reads only DNA. By introducing drugs that block the reverse transcriptase from completing the formation of viral DNA, HIV-1, replication can be stopped.

A number of compounds that interfere with viral replication have been developed to treat AIDS. For example, nucleoside analogs, such as 3'-azido-3'-deoxythymidine (AZT), 2',3'-dideoxycytidine (ddC), 2',3'-dideoxythymidinene (d4T), 2',3'-dideoxyinosine (ddI), and 2',3'-dideoxy-3'-thia-cytidine (3TC) have been shown to be relatively effective in halting HIV replication at the reverse transcriptase (RT) stage.

Even with the current success of reverse transcriptase inhibitors, it has been found that HIV patients can become resistant to a single inhibitor. Thus, it is desirable to develop additional inhibitors to further combat HIV infection and inhibit the replication of drug resistant strains of HIV.

SUMMARY OF THE INVENTION

It has now been discovered that oxindoles having novel structures effectively inhibit the replication of HIV, including drug resistant strains of the virus. Selected oxindoles of the invention are potent reverse transcriptase inhibitors. Accordingly, the present invention provides pharmaceutical compositions, and prophylactic and therapeutic treatments, diagnostic and prognostic methods and kits, and pharmaceutical screening methods that take advantage of the anti-HIV activity of the oxindoles.

Because the oxindoles of the invention inhibit HIV replication, the prophylactic or therapeutic administration of the oxindoles is a treatment for HIV infection. Prophylactic treatments are especially useful for persons at high risk of HIV infection. Thus, the present invention provides methods of inhibiting HIV replication in a person by administering to the person a pharmaceutically effective amount of an oxindole. This invention also provides pharmaceutical compositions comprising one or more oxindoles in a pharmaceutically acceptable carrier. The compounds of the invention can be administered orally, parentally (including subcutaneous injection, intravenous, intramuscular, intrasternal or infusion techniques), by inhalation spray, topically, by absorption through a mucous membrane, or rectally, in dosage unit formulations containing conventional non-toxic pharmaceutically acceptable carriers, adjuvants or vehicles.

Methods of inhibiting HIV replication described above can be applied to cells being cultured in vitro, as well.

In another aspect, the present invention provides a composition including at least one oxindole and a second therapeutic agent or agents. In an exemplary embodiment, the second therapeutic agent is used to prevent or treat HIV infection. In another embodiment, the second therapeutic agent is used to treat an opportunistic infection associated with HIV infection. The second therapeutic is, for example, a protease inhibitor, a non-nucleoside reverse transcriptase inhibitor, a nucleoside reverse transcriptase inhibitor, an antiretroviral nucleoside, an entry inhibitor, or any other anti-viral agent effective to inhibit or treat HIV infection. In another embodiment, the second therapeutic agent is selected from the group consisting of zidovudine, didanosine, stavudine, interferon, lamivudine, adefovir, nevirapine, delaviridine, loviride, saquinavir, indinavir, and AZT. In another embodiment, the second therapeutic agent is an antibiotic or acyclovir. In still a further embodiment, the second agent is selected from immunomodulators, and entry inhibitors.

In another aspect, the present invention provides methods of treating or preventing HIV infection in a human comprising administering an oxindole of the invention to a subject. As discussed above, the oxindole is optionally combined with one or more additional therapeutic agents.

The invention also provides oxindoles that are of use for inhibiting the replication of drug resistant, including multi-drug resistant, HIV mutants. The compounds of the invention have low cytotoxicity and display high potency against HIV and drug resistant strains of HIV. The compounds have been shown to inhibit replication of clinically observed drug resistant strains of HIV.

In another aspect, the present invention provides methods of inhibiting HIV infection in a CD4$^+$ culture comprising the step of contacting the cell with a oxindole of the invention, either alone or in combination with a second therapeutic agent or a combination of other therapeutic agents. In one embodiment, the therapeutic agent or agents are used to treat or prevent HIV infection.

Other aspects, objects and advantages of the invention will be apparent from the detailed description that follows.

DETAILED DESCRIPTION OF THE INVENTION AND PREFERRED EMBODIMENTS

General Overview

Figure 1E:
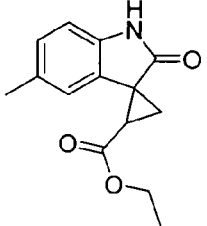
FIG. 1 is a table displaying exemplary compounds of the invention.

The present invention provides new compositions and methods for preventing or ameliorating viral, e.g., HIV infection, killing virally infected cells, e.g., HIV infected cells and generally, inhibiting viral, preferably HIV, replication. The present invention is, in part, based on the surprising discovery that the oxindoles of the invention effectively inhibit HIV infection, kill HIV infected cells and/or prevent HIV infection in the individual. Moreover, the compounds of the invention inhibit the replication of drug resistant strains of HIV.

The present invention provides compounds and pharmaceutical compositions that include those compounds. Moreover, the invention also provides methods of inhibiting HIV infection or replication by administering at least one compound of the invention to a patient in need of such treatment.

Definitions

"Reactive functional group," as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

"Non-covalent protein binding groups" are moieties that interact with an intact or denatured polypeptide in an associative manner. The interaction may be either reversible or irreversible in a biological milieu. The incorporation of a "non-covalent protein binding group" into an oxindole of the invention provides the compound with the ability to interact with a polypeptide in a non-covalent manner. Exemplary non-covalent interactions include hydrophobic-hydrophobic and electrostatic interactions. Exemplary "non-covalent protein binding groups" include anionic groups, e.g., phosphate, thiophosphate, phosphonate, carboxylate, boronate, sulfate, sulfone, thiosulfate, and thiosulfonate.

As used herein, "linking member" refers to a covalent chemical bond that includes at least one heteroatom. Exemplary linking members include —C(O)NH—, —C(O)O—, —NH—, —S—, —O—, and the like.

The term "targeting group" is intended to mean a moiety that is: (1) able to actively direct the entity to which it is attached (e.g., an oxindole) to a target region, e.g., an HIV infected cell; or (2) is preferentially passively absorbed by or entrained within a target tissue. The targeting group can be a small molecule, which is intended to include both non-peptides and peptides. The targeting group can also be a macromolecule, which includes, but is not limited to, saccharides, lectins, receptors, ligand for receptors, proteins such as BSA, antibodies, poly(ethers), dendrimers, poly (amino acids) and so forth.

The term "cleavable group" is intended to mean a moiety that allows for release of an oxindole from a conjugate by cleaving a bond linking the oxindole (or oxindole linker arm construct) to the remainder of the conjugate. Such cleavage is either chemical in nature, or enzymatically mediated. Exemplary enzymatically cleavable groups include natural amino acids or peptide sequences that end with a natural amino acid.

In addition to enzymatically cleavable sites, it is within the scope of the present invention to include one or more sites that are cleaved by the action of an agent other than an enzyme. Exemplary non-enzymatic cleavage agents include, but are not limited to, acids, bases, light (e.g., nitrobenzyl derivatives, phenacyl groups, benzoin esters), and heat. Many cleaveable groups are known in the art. See, for example, Jung et al., *Biochem. Biophys. Acta,* 761: 152–162 (1983); Joshi et al., *J. Biol. Chem.,* 265: 14518–14525 (1990); Zarling et al., *J. Immunol.,* 124: 913–920 (1980); Bouizar et al., *Eur. J. Biochem.,* 155: 141–147 (1986); Park et al., *J. Biol. Chem.,* 261: 205–210 (1986); Browning et al., *J. Immunol.,* 143: 1859–1867 (1989). Moreover a broad range of cleavable, bifunctional (both homo- and hetero-bifunctional) spacer arms are commercially available from suppliers such as Pierce.

The symbol ⁓, whether utilized as a bond or displayed perpendicular to a bond indicates the point at which the displayed moiety is attached to the remainder of the molecule, solid support, etc.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the invention may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), VOGEL'S ENCYCLOPEDIA OF PRACTICAL ORGANIC CHEMISTRY $5^{TH}$ ED., Longman Scientific and Technical Ltd., Essex, 1991, pp. 809–816; and Heller, *Acc. Chem. Res.* 23: 128 (1990).

The compounds of the present invention may also contain unnatural proportions of atomic isotopes at one or more of the atoms that constitute such compounds. For example, the compounds may be radiolabeled with radioactive isotopes, such as for example tritium (3H), iodine-125 ($^{125}I$) or carbon-14 ($^{14}C$). All isotopic variations of the compounds of the present invention, whether radioactive or not, are intended to be encompassed within the scope of the present invention.

Where substituent groups are specified by their conventional chemical formulae, written from left to right, they equally encompass the chemically identical substituents, which would result from writing the structure from right to left, e.g., —$CH_2O$— is intended to also recite —$OCH_2$—.

The term "alkyl," by itself or as part of another substituent means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$–$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —$Si(CH_3)_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—$Si(CH_3)_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$C(O)_2R'$— represents both —$C(O)_2R'$— and —$R'C(O)_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo $(C_1-C_4)$alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R" R'", —OC(O)R', —C(O)R', —CO$_2$R', —CONR'R", —OC(O)NR"R", —NR"C(O)R', —NR'—C(O)NR"R'", —NR"C(O)$_2$R', —NR—C(NR'R" R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1–3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R" R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R" R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro($C_1-C_4$)alkoxy, and fluoro($C_1-C_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present. In the schemes that follow, the symbol X represents "R" as described above.

Two of the substituents on adjacent atoms of the aryl or heteroaryl ring may optionally be replaced with a substituent of the formula -T-C(O)—(CRR')$_q$-U-, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A—(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted ($C_1-C_6$)alkyl.

As used herein, the term "heteroatom" is meant to include oxygen (O), nitrogen (N), sulfur (S) and silicon (Si).

"Protecting group," as used herein refers to a portion of a substrate that is substantially stable under a particular reaction condition, but which is cleaved from the substrate under a different reaction condition. A protecting group can also be selected such that it participates in the direct oxidation of the aromatic ring component of the compounds of the invention. For examples of useful protecting groups, see, for example, Greene et al., PROTECTIVE GROUPS IN ORGANIC SYNTHESIS, John Wiley & Sons, New York, 1991.

As used herein, "pharmaceutically acceptable salt" refers to a salt that retains the desired biological activity of the parent compound and does not impart any undesired toxicological effects. Examples of such salts include, but are not limited to, (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalenedisulfonic acids, polygalacturonic acid; (b) salts with polyvalent metal cations such as zinc, calcium, bismuth, barium, magnesium, aluminum, copper, cobalt, nickel, cadmium, and the like; or (c) salts formed with an organic cation formed from N,N'-dibenzylethylenediamine or ethylenediamine; or (d) combinations of (a) and (b) or (c), e.g., a zinc tannate salt; and the like. The preferred acid addition salts are the trifluoroacetate salt and the acetate salt.

A "disorder associated with HIV infection" or "disease associated with HIV infection" refers to a disease state which is marked by HIV infection. Such disorders associated with HIV infection include, but are not limited to, AIDS, Kaposi's sarcoma, opportunistic infections such as those caused by *Pneumocystis carinii* and *Mycobacterium tuberculosis*; oral lesions, including thrush, hairy leukoplakia, and aphthous ulcers; generalized lymphadenopathy, shingles, thrombocytopenia, aseptic meningitis, and neurologic disease such as toxoplasmosis, cryptococcosis, CMV infection, primary CNS lymphoma, and HIV-associated dementia, peripheral neuropathies, seizures, and myopathy.

As used herein, "reverse transcriptase (RT) activity" means the ability to effect reverse transcription of retroviral RNA to proviral DNA. One means by which RT activity can be determined is by measuring viral replication. One measure of HIV-1 viral replication is the p24 core antigen enzyme immunoassay, for example, using the assay commercially available from Coulter Corporation/Immunotech, Inc. (Westbrooke, Mich.). Another means by which RT activity is analyzed is by assay of recombinant HIV-1 reverse transcriptase (rRT) activity, for example, using the Quan-T-RT assay system commercially available from Amersham (Arlington Heights, Ill.) and described in Bosworth, et al., *Nature*, 1989, 341:167–168.

As used herein, "HIV reverse transcriptase inhibitor" is intended to refer to both nucleoside and non-nucleoside inhibitors of HIV reverse transcriptase (RT). Examples of nucleoside RT inhibitors include, but are not limited to, AZT, ddC, ddI, d4T, and 3TC. Examples of non-nucleoside RT inhibitors include, but are no limited to, delavirdine (Pharmacia and Upjohn U90152S), efavirenz (DuPont), nevirapine (Boehringer Ingelheim), Ro 18,893 (Roche), trovirdine (Lilly), MKC-442 (Triangle), HBY 097 (Hoechst), ACT (Korean Research Institute), UC-781 (Rega Institute), UC-782 (Rega Institute), RD4-2025 (Tosoh Co. Ltd.), and MEN 10979 (Menarini Farmaceutici).

As used herein, "HIV protease inhibitor" is intended to refer to compounds that inhibit HIV protease. Examples include, but are not limited, saquinavir (Roche, Ro31-8959), ritonavir (Abbott, ABT-538), indinavir (Merck, MK-639), amprenavir (Vertex/Glaxo Wellcome), nelfinavir (Agouron, AG-1343), palinavir (Boehringer Ingelheim), BMS-232623 (Bristol-Myers Squibb), GS3333 (Gilead Sciences), KNI-413 (Japan Energy), KNI-272 (Japan Energy), LG-71350 (LG Chemical), CGP-61755 (Ciba-Geigy), PD 173606 (Parke Davis), PD 177298 (Parke Davis), PD 178390 (Parke Davis), PD 178392 (Parke Davis), U-140690 (Pharmacia and Upjohn), and ABT-378. Additional examples include the cyclic protease inhibitors disclosed in WO93/07128, WO 94/19329, WO 94/22840, and PCT Application Number US96/03426.

As used herein, a compound that "inhibits replication of human immunodeficiency virus (HIV)" means a compound that, when contacted with HIV, for example, via HIV-infected cells, effects a reduction in the amount of HIV as compared with untreated control. Inhibition of replication of HIV can be measured by various means known in the art, for example, the p24 assay.

By "therapeutically effective dose" herein is meant a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1–3, 1992); Lloyd, *The Art, Science and Technology of Pharmaceutical Compounding* (1999); and Pickar, *Dosage Calculations* (1999)).

"Mutant HIV" means a strain of HIV having one or more mutated or altered amino acids as compared with wild type.

"Multi-Drug Resistant HIV" means one or more HIV strain that is resistant to treatment with one or more chemotherapeutic agent.

Compounds

In a first aspect, the invention provides oxindoles and related compounds. Exemplary compounds of the invention are set forth below:

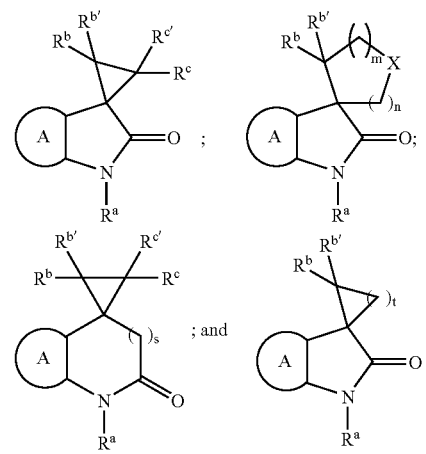

in which the symbol A represents a ring system that is selected from substituted or unsubstituted aryl and substituted or unsubstituted heteroaryl. The symbols m, n and s represent integers that are independently selected from 0, 1 and 2. Also provided are pharmaceutically acceptable salts of the compounds set forth above.

The symbols $R^a$, $R^b$, $R^{b'}$, $R^c$, and $R^{c'}$ represent members independently selected from H, substituted or unsubstituted alkyl, substituted or unsubstituted cycloalkyl, substituted or unsubstituted heteroalkyl, substituted or unsubstituted aryl, substituted or unsubstituted heteroaryl, or another "alkyl substituent" as defined hereinabove. Additional information regarding the identities of the "R" groups, above, is provided in the succeeding paragraphs.

In an exemplary embodiment, the invention provides compounds according to Formula I:

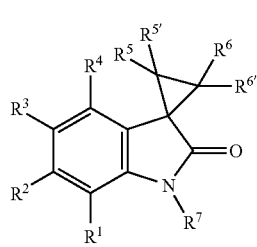

(I)

in which the symbols $R^1$, $R^2$, $R^3$ and $R^4$ independently represent H, substituted or unsubstituted alkyl, substituted or unsubstituted heteroalkyl, substituted or unsubstituted aryl, substituted or unsubstituted heteroaryl, $OR^8$, $NO_2$, CN or halogen. The symbol $R^8$ represents H or substituted or unsubstituted alkyl.

The symbols $R^5$ and $R^{5'}$ represent H, substituted or unsubstituted alkyl, substituted or unsubstituted cycloalkyl, substituted or unsubstituted heteroalkyl, substituted or unsubstituted aryl, substituted or unsubstituted heteroaryl, CN, $SR^9$, $C(O)R^9$. $R^9$ is H, substituted or unsubstituted alkyl, substituted or unsubstituted heteroalkyl, substituted or unsubstituted aryl, $NR^{10}R^{11}$ or $OR^{11}$. $R^{10}$ is H, substituted or unsubstituted alkyl and $OR^{12}$. The symbol $R^{12}$ represents H, substituted or unsubstituted alkyl or substituted or unsubstituted heteroalkyl. $R^{11}$ is selected from H, $C(O)R^{13}$, substituted or unsubstituted alkyl, substituted or unsubstituted heteroalkyl, substituted or unsubstituted aryl and substituted or unsubstituted heterocycloalkyl. In an exemplary embodiment, $R^{11}$ is substituted or unsubstituted benzyl.

The groups, $R^{10}$ and $R^{11}$, together with the nitrogen to which they are bound, are optionally joined to form a heterocycloalkyl ring system having from 3 to 7 members. The heterocycloalkyl ring is substituted or unsubstituted. In an exemplary embodiment the ring is substituted with one or more substituted or unsubstituted alkyl moieties. The symbol $R^{13}$ represents H, substituted or unsubstituted alkyl, substituted or unsubstituted heteroalkyl and $NR^{14}R^{15}$. $R^{14}$ and $R^{15}$ are independently selected from H, substituted or unsubstituted alkyl and substituted or unsubstituted heteroalkyl.

The symbols $R^6$ and $R^{6'}$ independently represent H, substituted or unsubstituted alkyl (e.g., substituted or unsubstituted $C_1$–$C_6$ alkyl) and $C(O)R^{16}$. $R^{16}$ is substituted or unsubstituted alkyl, substituted or unsubstituted heteroalkyl, $NR^{17}R^{18}$ or $OR^{17}$. The symbols $R^{17}$ and $R^{18}$ represent moieties that are independently selected from H, substituted or unsubstituted alkyl, substituted or unsubstituted heteroalkyl and substituted or unsubstituted aryl.

$R^7$ is H, substituted or unsubstituted alkyl or substituted or unsubstituted heteroalkyl.

In an exemplary embodiment according to Formula II, at least one of $R^5$ and $R^{5'}$ is substituted or unsubstituted phenyl, substituted or unsubstituted pyridyl, substituted or unsubstituted furanyl, substituted or unsubstituted benzofuranyl or substituted or unsubstituted thienyl.

In another exemplary embodiment, the invention provides compounds according to Formula II:

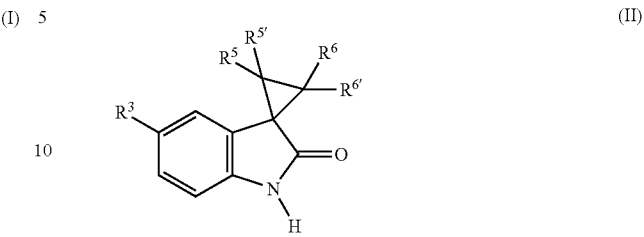

(II)

in which the identity of each of the radicals is substantially as described above.

In selected compounds according to Formula II, at least one of $R^5$ and $R^{5'}$ is a member selected from a substituted or unsubstituted heteroaryl ring, such as:

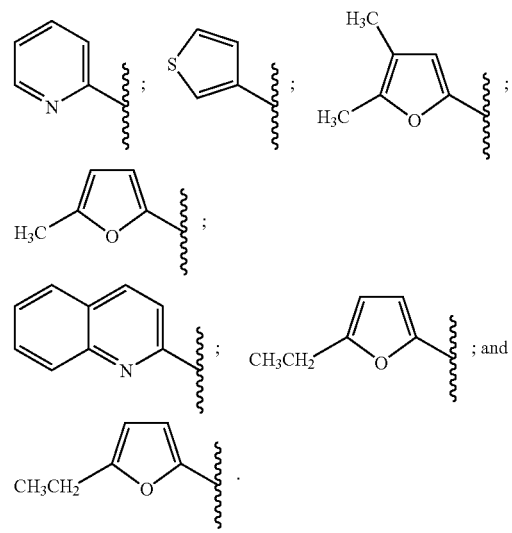

A list of exemplary substituents for aryl and heteroaryl moieties is found in the definitions section provided herein. When the heteroaryl ring is substituted, it can be substituted at any position or at multiple positions on the ring. When more than one substituent is present, the substituents can be either the same or different.

In a further exemplary embodiment, the invention provides compounds according to Formula III:

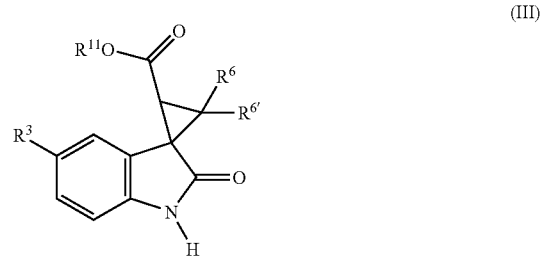

(III)

in which the identity of each of the radicals is substantially as described above.

In selected compounds according to Formula III, $R^{11}$ is substituted or unsubstituted $C_1$–$C_4$ alkyl.

In a still further exemplary embodiment, the invention provides compounds according to Formulae II and III in which $R^6$ and $R^{6'}$ are independently selected from substituted or unsubstituted methyl and substituted or unsubstituted ethyl.

In another exemplary embodiment, at least one of $R^1$–$R^7$ is a moiety that increases the water-solubility of the parent compound. Exemplary moieties of use for increasing a compound's water solubility include ethers and polyethers, e.g., a member selected from ethylene glycol, and ethylene glycol oligomers, having a molecular weight of from about 60 daltons to about 10,000 daltons, and more preferably of from about 100 daltons to about 1,000 daltons.

Representative polyether-based substituents include, but are not limited to, the following structures:

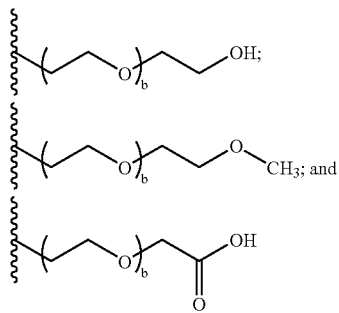

in which b is preferably a number from 1 to 100, inclusive. Functionalized polyethers are known to those of skill in the art and many are commercially available from, for example, Shearwater Polymers, Inc. (Alabama).

In another exemplary embodiment, at least one of $R^1$–$R^7$ is a linker moiety that includes a reactive functional group for conjugating the compound to another molecule or to a surface. The linkers of use in the compounds of the invention can also include a cleaveable group. In an exemplary embodiment, the cleaveable group is interposed between the oxindole core and a targeting agent or macromolecular backbone. Representative useful reactive groups are discussed in greater detail in succeeding sections. Information concerning reactive groups is known to those of skill in the art. See, for example, Hermanson, BIOCONJUGATE TECHNIQUES, Academic Press, San Diego, 1996.

Reactive Functional Groups

As discussed above, the oxindole core of the compounds of the invention are optionally tethered to other species by means of bonds formed between a reactive functional group on the oxindole or a linker attached to the oxindole, and a reactive functional group of complementary reactivity on the other species. For clarity of illustration the succeeding discussion focuses on the conjugation of representative oxindoles of the invention to polymers, including poly (ethers) and dendrimers, and to targeting agents useful for translocating the oxindole-targeting agent conjugate across a membrane. The focus exemplifies selected embodiments of the invention from which others are readily inferred by one of skill in the art. No limitation of the invention is implied, by focusing the discussion on the representative embodiments.

Exemplary oxindoles of the invention bear a reactive functional group, which is generally located on the oxindole ring or on a substituted or unsubstituted alkyl or heteroalkyl chain attached to the ring, allowing their facile attachment to another species. A convenient location for the reactive group is the terminal position of an alkyl or heteroalkyl substituent of the oxindole core.

Reactive groups and classes of reactions useful in practicing the present invention are generally those that are well known in the art of bioconjugate chemistry. Currently favored classes of reactions available with reactive analogues are those proceeding under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Exemplary reaction types include the reaction of carboxyl groups and various derivatives thereof including, but not limited to, N-hydroxysuccinimide esters, N-hydroxybenzotriazole esters, acid halides, acyl imidazoles, thioesters, p-nitrophenyl esters, alkyl, alkenyl, alkynyl and aromatic esters. Hydroxyl groups can be converted to esters, ethers, aldehydes, etc. Haloalkyl groups are converted to new species by reaction with, for example, an amine, a carboxylate anion, thiol anion, carbanion, or an alkoxide ion. Dienophile (e.g., maleimide) groups participate in Diels-Alder. Aldehyde or ketone groups can be converted to imines, hydrazones, semicarbazones or oximes, or reacted via such mechanisms as Grignard addition or alkyllithium addition. Sulfonyl halides react readily with amines, for example, to form sulfonamides. Amine or sulfhydryl groups are, for example, acylated, alkylated or oxidized. Alkenes can be converted to an array of new species using cycloadditions, acylation, Michael addition, etc. Epoxides react readily with amines and hydroxyl compounds.

Exemplary combinations of reactive functional groups found on a ligand of the invention and on a targeting moiety (or polymer or linker) are set forth in Table 1.

TABLE 1

| Chemical Functionality 1 | Chemical Functionality 2 | Linkage |
|---|---|---|
| Hydroxy | Carboxy | Ester |
|  | Hydroxy | Carbonate |
|  | Amine | Carbamate |
|  | $SO_3$ | Sulfate |
|  | $PO_3$ | Phosphate |
|  | Carboxy | Acyloxyalkyl |
|  | Ketone | Ketal |
|  | Aldehyde | Acetal |
|  | Hydroxy | Anhydride |
| Mercapto | Mercapto | Disulfide |
|  | Carboxy | Acyloxyalkyl Thioether |
|  | Carboxy | Thioester |
|  | Carboxy | Amino amide |
|  | Mercapto | Thioester |
|  | Carboxy | Acyloxyalkyl ester |
|  | Carboxy | Acyloxyalkyl amide |
|  | Amino | Acyloxyalkoxy carbonyl |

TABLE 1-continued

| Chemical Functionality 1 | Chemical Functionality 2 | Linkage |
|---|---|---|
| | Carboxy | Anhydride |
| | Carboxy | N-acylamide |
| | Hydroxy | Ester |
| | Hydroxy | Hydroxymethyl ketone ester |
| | Hydroxy | Alkoxycarbonyl oxyalkyl |
| Amino | Carboxy | Acyloxyalkylamine |
| | Carboxy | Acyloxyalkylamide |
| | Amino | Urea |
| | Carboxy | Amide |
| | Carboxy | Acyloxyalkoxycarbonyl |
| | Amide | N-Mannich base |
| | Carboxy | Acyloxyalkyl carbamate |
| Phosphate oxygen ester | Hydroxy | Phosphate |
| | Amine | Phosphoramidate |
| | Mercapto | Thiophosphate ester |
| Ketone | Carboxy | Enol ester |
| Sulfonamide | Carboxy | Acyloxyalkyl sulfonamide |
| | Ester | N-sulfonyl-imidate |

One skilled in the art will readily appreciate that many of these linkages may be produced in a variety of ways and using a variety of conditions. For the preparation of esters, see, e.g., March supra at 1157; for thioesters, see, March, supra at 362–363, 491, 720–722, 829, 941, and 1172; for carbonates, see, March, supra at 346–347; for carbamates, see, March, supra at 1156–57; for amides, see, March supra at 1152; for ureas and thioureas, see, March supra at 1174; for acetals and ketals, see, Greene et al. supra 178–210 and March supra at 1146; for acyloxyalkyl derivatives, see, PRODRUGS: TOPICAL AND OCULAR DRUG DELIVERY, K. B. Sloan, ed., Marcel Dekker, Inc., New York, 1992; for enol esters, see, March supra at 1160; for N-sulfonylimidates, see, Bundgaard et al., *J. Med. Chem.*, 31:2066 (1988); for anhydrides, see, March supra at 355–56, 636–37, 990–91, and 1154; for N-acylamides, see, March supra at 379; for N-Mannich bases, see, March supra at 800–02, and 828; for hydroxymethyl ketone esters, see, Petracek et al. *Annals NY Acad. Sci.*, 507:353–54 (1987); for disulfides, see, March supra at 1160; and for phosphonate esters and phosphonamidates.

The reactive functional groups can be chosen such that they do not participate in, or interfere with, the reactions necessary to assemble the reactive ligand analogue. Alternatively, a reactive functional group can be protected from participating in the reaction by the presence of a protecting group. Those of skill in the art will understand how to protect a particular functional group from interfering with a chosen set of reaction conditions. For examples of useful protecting groups, see Greene et al., PROTECTIVE GROUPS IN ORGANIC SYNTHESIS, John Wiley & Sons, New York, 1991.

Generally, prior to forming the linkage between the ligand and the targeting (or other) agent, and optionally, the linker group, at least one of the chemical functionalities is activated. One skilled in the art will appreciate that a variety of chemical functionalities, including hydroxy, amino, and carboxy groups, can be activated using a variety of standard methods and conditions. For example, a hydroxyl group of the ligand (or targeting agent) can be activated through treatment with phosgene to form the corresponding chloroformate, or p-nitrophenylchloroformate to form the corresponding carbonate.

In an exemplary embodiment, the invention makes use of a targeting agent that includes a carboxyl functionality. Carboxyl groups may be activated by, for example, conversion to the corresponding acyl halide or active ester. This reaction may be performed under a variety of conditions as illustrated in March, supra pp. 388–89. In an exemplary embodiment, the acyl halide is prepared through the reaction of the carboxyl-containing group with oxalyl chloride. The activated agent is combined with a ligand or ligand-linker arm combination to form a conjugate of the invention. Those of skill in the art will appreciate that the use of carboxyl-containing targeting agents is merely illustrative, and that agents having many other functional groups can be conjugated to the ligands of the invention.

Targeting Groups

The compounds of the invention may also be conjugated to an agent that targets the compound to a specific tissue or region of disease. The compound of the invention can be targeted for specific delivery to the cells to be treated by conjugation of the compounds to a targeting agent. The term "targeting agent" refers to a species that serves to deliver the compound of the invention to a specific site. Targeting agents include, for example, molecules that specifically bind molecules present on a cell surface. Such targeting agents useful in the invention include anti-cell surface antigen antibodies; cytokines, including interleukins, factors such as epidermal growth factor (EGF), and the like, are also specific targeting agents known to bind cells expressing high levels of their receptors. Targeting agents include species that are taken up by cells using either active or passive mechanisms.

Particularly useful targeting agents for targeting the compounds of the invention to cells for therapeutic activity include those ligands that bind antigens or receptors present on virus-infected cells to be treated. For example, antigens present on T-cells, such as CD48, can be targeted with antibodies. Antibody fragments, including single chain fragments, can also be used. Other such ligand-receptor binding pairs are known in the scientific literature for targeting anti-viral treatments to target cells. Methods for producing conjugates of the compounds of the invention and the targeting moieties are known.

Membrane translocation polypeptides are another exemplary targeting agent. Membrane translocation polypeptides" have amphiphilic or hydrophobic amino acid subsequences that have the ability to act as membrane-translocating carriers. In one embodiment, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, *Current Opinion in Neurobiology* 6:629–634 (1996)). Another subsequence, the h (hydrophobic) domain of signal peptides, was found to have similar cell membrane translocation characteristics (see, e.g., Lin et al., *J. Biol. Chem.* 270:1 4255–14258 (1995)).

Examples of peptide sequences include, but are not limited to: an 11 amino acid peptide of the tat protein of HIV; a 20 residue peptide sequence which corresponds to amino acids 84–103 of the p16 protein (see Fahraeus et al., *Current Biology* 6:84 (1996)); the third helix of the 60-amino acid long homeodomain of Antennapedia (Derossi et al., *J. Biol. Chem.* 269:10444 (1994)); the h region of a signal peptide such as the Kaposi fibroblast growth factor (K-FGF) h region (Lin et al., supra); or the VP22 translocation domain from HSV (Elliot & O'Hare, *Cell* 88:223–233 (1997)). Other suitable chemical moieties that provide enhanced cellular uptake may also be chemically linked to the compounds of the invention.

Such subsequences can be used to translocate compounds of the invention across a cell membrane. Compounds of the invention can be conveniently fused to or derivatized with such sequences. Typically, the translocation sequence is provided as part of a fusion protein. Optionally, a linker as described herein can be used to link the compound of the invention and the translocation sequence. Any suitable linker can be used, e.g., a peptide linker or other chemical linkers.

Toxin molecules also have the ability to transport compounds across cell membranes. Often, such molecules are composed of at least two parts (called "binary toxins"): a translocation or binding domain or polypeptide and a separate toxin domain or polypeptide. Typically, the translocation domain or polypeptide binds to a cellular receptor, and then the toxin is transported into the cell. Several bacterial toxins, including *Clostridium perfringens* iota toxin, diphtheria toxin (DT), Pseudomonas exotoxin A (PE), pertussis toxin (PT), *Bacillus anthracis* toxin, and pertussis adenylate cyclase (CYA), have been used in attempts to deliver peptides to the cell cytosol as internal or amino-terminal fusions (Arora et al., *J. Biol. Chem.*, 268:3334–3341 (1993); Perelle et al., *Infect. Immun.*, 61:5147–5156 (1993); Stenmark et al., *J. Cell Biol.* 113:1025–1032 (1991); Donnelly et al., *PNAS* 90:3530–3534 (1993); Carbonetti et al., *Abstr. Annu. Meet. Am. Soc. Microbiol.* 95:295 (1995); Sebo et al., *Infect. Immun.* 63:3851–3857 (1995); Klimpel et al., *PNAS U.S.A.* 89:10277–10281 (1992); and Novak et al., *J. Biol. Chem.* 267:17186–17193 1992)).

Non-covalent protein binding groups are also of use to target the compounds of the invention to specific regions of the body and to increase the half-life of the agent through protein binding.

Macromolecular Conjugates

In an exemplary embodiment, the invention provides a macromolecular, i.e., MW>1000 D, conjugate between the oxindole core and a macromolecular species. In one embodiment, a macromolecular conjugate of the invention is formed by covalently conjugating an oxindole to a macromolecule via a reactive functional group. In another embodiment, the macromolecular conjugate is formed by a non-covalent interaction between an oxindole derivative and a macromolecule, e.g, a serum protein.

In the following discussion, the invention is described by reference to specific macromolecules of use for forming conjugates with the novel oxindole cores of the invention. Those of skill in the art will appreciate that the focus of the discussion is for clarity of illustration and does not limit the scope of the invention. The invention provides macromolecular conjugates that include components derived from biomolecules and synthetic molecules. Exemplary biomolecules include polypeptides (e.g., antibodies, enzymes, receptors, antigens); polysaccharides (e.g., starches, inulin, dextran); lectins, non-peptide antigens and the like. Exemplary synthetic polymers include poly(acrylic acid), poly (lysine), poly(glutamic acid), poly(ethylene imine), etc.

Covalent Conjugation

Selection of an appropriate reactive functional group on an oxindole core of the invention to form a desired macromolecular species is well within the abilities of one of skill in the art. Exemplary reactive functional groups of use in forming the covalent conjugates of the invention are discussed above. It is well within the abilities of one of skill to select and prepare an oxindole core of the invention having an appropriate reactive functional group of complementary reactivity to a reactive group on its conjugation partner.

In one embodiment, the bond formed between reactive functional groups of the macromolecule and that of the oxindole attaches the oxindole to the macromolecule essentially irreversibly via a "stable bond" between the components. A "stable bond", as used herein, is a bond, which maintains its chemical integrity over a wide range of conditions (e.g., amide, carbamate, carbon-carbon, ether, etc.). In another embodiment, a "cleaveable bond" links the macromolecule and the oxindole. A "cleaveable bond", as used herein, is a bond that undergoes scission under selected conditions. Cleaveable bonds include, but are not limited to, disulfide, imine, carbonate and ester bonds. As discussed in the preceding sections, the reactive functional group can be located at one or more positions of the oxindole.

Polysaccharides

In an exemplary embodiment, the present invention provides conjugates between an oxindole core and saccharides, e.g., polysaccharides. In an exemplary embodiment, the invention provides a conjugate between an oxindole and inulin. Inulin is a naturally occurring polysaccharide, which has been previously investigated as a carrier for diagnostic moieties (Rongved, P. K., *J. Carbohydr. Res.* 1991, 214, 315; Corsi, D. M. V. E. et al., *Chem. Eur. J.* 2001, 7, 64). The structure of inulin can be described as a mixture of linear β-(2→1)-linked α-D-fructofuranosyl chains with a α-D-glucopyranosyl unit at the terminal end. Inulin is commercially available in a variety of molecular weights and the degree of polymerization varies from 10 to 30, resulting in a molecular weight distribution of 1500 to 5000 Da. The high hydrophilicity, pH stability, low solution viscosity and biocompatability of inulin ensure that its conjugates have favorable pharmacological properties.

Dendrimer-Based Agents

In another aspect, the present invention provides an oxindole as set forth above, which is attached to a dendrimer via a reactive functional group. Similar to the polymeric group discussed above, the dendrimer has at least two reactive functional groups. In one embodiment, one or more formed oxindole is attached to the dendrimer. Alternatively, the oxindole is formed directly on the dendrimer.

In an exemplary embodiment, a water-soluble and bio-adapted polyester (polypropionate) class of dendrimers has been designed to provide favorable pharmacokinetic properties. See, for example, Ihre, H. et al., *Macromolecules* 1998, 31, 4061; Ihre, H. et al., *J. Am. Chem. Soc.* 1996, 118, 6388; Anders, H., Ihre, H., Patent WO/9900440 (Sweden)). In an exemplary embodiment, the termini of the dendrimers are conjugated to an oxindole core of the invention.

Poly(ethylene glycol)-Based Agents

In another exemplary embodiment, the invention provides a conjugate between an oxindole core of the invention and poly(ethylene glycol). Poly(ethylene glycol) (PEG) is used in biotechnology and biomedical applications. The use of this agent has been reviewed (POLY(ETHYLENE GLYCOL) CHEMISTRY: BIOTECHNICAL AND BIOMEDICAL APPLICATIONS, J. M. Harris, Ed., Plenum Press, New York, 1992). Modification of enzymes (Chiu et al., *J. Bioconjugate Chem.*, 4: 290–295 (1993)), RGD peptides (Braatz et al., *Bioconjugate Chem.*, 4: 262–267 (1993)), liposomes (Zalipsky, *S. Bioconjugate Chem.*, 4: 296–299 (1993)), and CD4-IgG glycoprotein (Chamow et al., *Bioconjugate Chem.*, 4: 133–140 (1993)) are some of the recent advances in the use of polyethylene glycol. Surfaces treated with PEG have been shown to resist protein deposition and have improved resistance to thrombogenicity when coated on blood contacting biomaterials (Merrill, "Poly(ethylene oxide) and Blood Contact: A Chronicle of One Laboratory," in POLY(ETHYLENE GLYCOL) CHEMISTRY: BIOTECHNICAL AND BIOMEDICAL APPLICATIONS, Harris, Ed., Plenum Press, New York, (1992), pp. 199–220).

Many routes are available for attaching an oxindole core of the invention onto a polymeric or oligomeric species. See, for example, Dunn, R. L., et al., Eds. POLYMERIC DRUGS AND DRUG DELIVERY SYSTEMS, ACS Symposium Series Vol. 469, American Chemical Society, Washington, D.C. 1991; Herren et al., *J. Colloid and Interfacial Science* 115: 46–55 (1987); Nashabeh et al., *J. Chromatography* 559: 367–383 (1991); Balachandar et al., *Langmuir* 6: 1621–1627 (1990); and Burns et al., *Biomaterials* 19: 423–440 (1998).

Many activated derivatives of poly(ethyleneglycol) are available commercially and in the literature. It is well within the abilities of one of skill to choose, and synthesize if necessary, an appropriate activated PEG derivative with which to prepare a conjugate useful in the present invention. See, Abuchowski et al. *Cancer Biochem. Biophys.*, 7: 175–186 (1984); Abuchowski et al., *J. Biol. Chem.*, 252: 3582–3586 (1977); Jackson et al., *Anal. Biochem.*, 165: 114–127 (1987); Koide et al., *Biochem Biophys. Res. Commun.*, 111: 659–667 (1983)), tresylate (Nilsson et al., *Methods Enzymol.*, 104: 56–69 (1984); Delgado et al., *Biotechnol. Appl. Biochem.*, 12: 119–128 (1990)); N-hydroxysuccinimide derived active esters (Buckmann et al., *Makromol. Chem.*, 182: 1379–1384 (1981); Joppich et al., *Makromol. Chem.*, 180: 1381–1384 (1979); Abuchowski et al., *Cancer Biochem. Biophys.*, 7: 175–186 (1984); Katre et al. *Proc. Natl. Acad. Sci. U.S.A.*, 84: 1487–1491 (1987); Kitamura et al., *Cancer Res.*, 51: 4310–4315 (1991); Boccu et al., *Z. Naturforsch.*, 38C: 94–99 (1983), carbonates (Zalipsky et al., POLY(ETHYLENE GLYCOL) CHEMISTRY: BIOTECHNICAL AND BIOMEDICAL APPLICATIONS, Harris, Ed., Plenum Press, New York, 1992, pp. 347–370; Zalipsky et al., *Biotechnol. Appl. Biochem.*, 15: 100–114 (1992); Veronese et al., *Appl. Biochem. Biotech.*, 11: 141–152 (1985)), imidazolyl formates (Beauchamp et al., *Anal. Biochem.*, 131: 25–33 (1983); Berger et al., *Blood,* 71: 1641–1647 (1988)), 4-dithiopyridines (Woghiren et al., *Bioconjugate Chem.*, 4: 314–318 (1993)), isocyanates (Byun et al., *ASAIO Journal*, M649-M-653 (1992)) and epoxides (U.S. Pat. No. 4,806, 595, issued to Noishiki et al., (1989). Other linking groups include the urethane linkage between amino groups and activated PEG. See, Veronese, et al., *Appl. Biochem. Biotechnol.*, 11: 141–152 (1985).

Synthesis and Purification of Oxindoles

The compounds of the invention are synthesized by an appropriate combination of generally well-known synthetic methods. Techniques useful in synthesizing the compounds of the invention are both readily apparent and accessible to those of skill in the relevant art. The discussion below is offered to illustrate certain of the diverse methods available for use in assembling the compounds of the invention, it is not intended to define the scope of reactions or reaction sequences that are useful in preparing the compounds of the present invention. Exemplary reaction schemes leading to the formation of oxindoles of the invention are set forth in the schemes below.

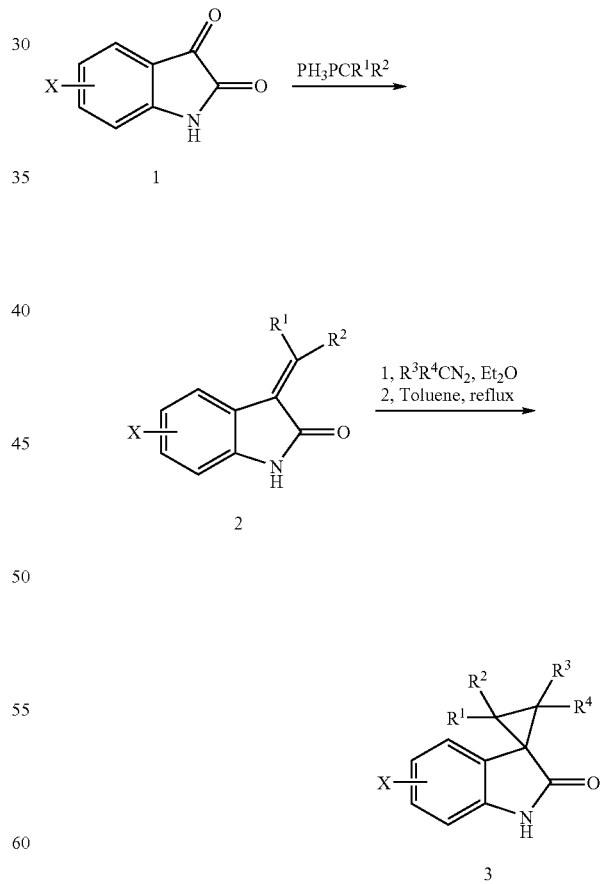

One method of synthesizing compounds of the invention is set forth in Scheme 1, wherein the cyclopropyl oxindole 3 is prepared. In the first step, the carboxyl oxindole 1 is reacted with an ylide reagent to form the corresponding alkene oxindole 2. Carbene transfer to 2 is accomplished using a diazirine in ether to form the cyclopropyl oxindole 3. One skilled in the art will recognize that derivatization of the cyclopropyl oxindole may be accomplished by modifying the substituents in the ylide and/or the diazirine.

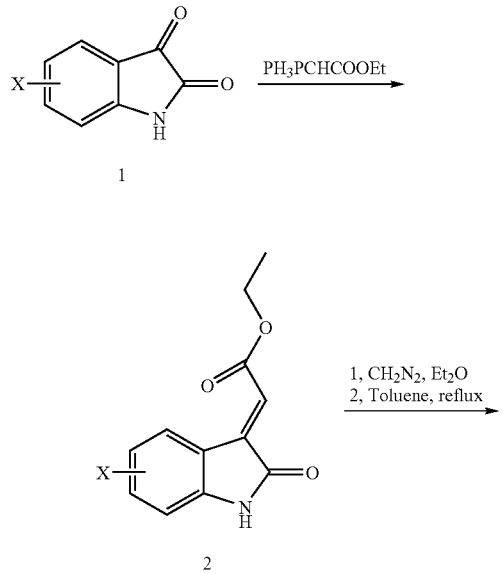

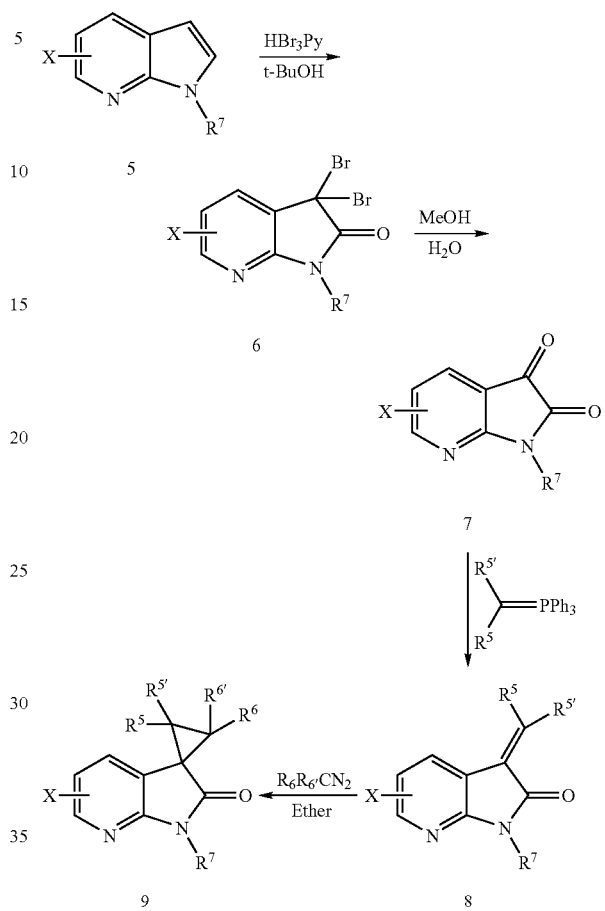

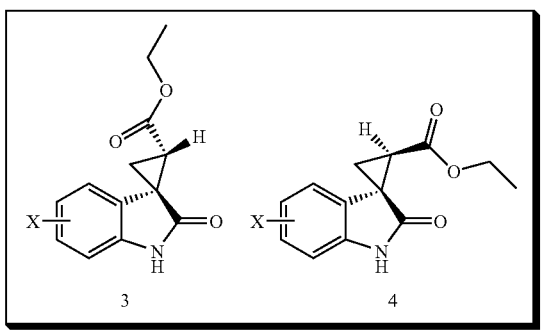

As set forth in Scheme 3, the double bond of the five-member ring of the fused heterocyclic ring system of 5 is converted to gem-dibromo-lactam 6. The gem-dibromo moiety is transformed to a carbonyl group, providing 7. The carbonyl moiety α to the pyridine moiety is converted to a double bond using an ylide reagent to produce 8, which is subsequently cyclized to cyclopropyl derivative 9.

Scheme 4 sets forth an exemplary route for preparing compounds of the invention in which the cyclopropyl ring is replaced with a heterocyclic ring. Scheme 4a illustrates a route to a nitrogen-containing heterocycle. Scheme 4b provides a route to an oxygen-containing heterocycle.

In a further exemplary synthesis, Scheme 2 illustrates the formation of an oxindole that includes an ethyl ester substituent on the cyclopropyl oxindole. The carboxyl oxindole is reacted with an ethyl ester ylide to form the carboxyl ester oxindole 2. Diazomethane is then used to transfer a methylene to 2 to form stereoisomers of the corresponding ethyl ester cyclopropyl oxindole 3 and 4.

A further exemplary synthesis to compounds of the invention in which ring system A is a heterocycle is set forth below in Scheme 3, in which the synthesis is exemplified by the use of a pyridyl system for ring system A.

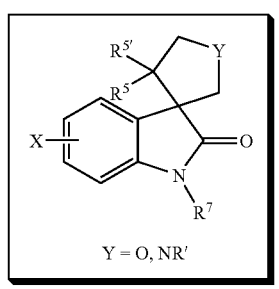

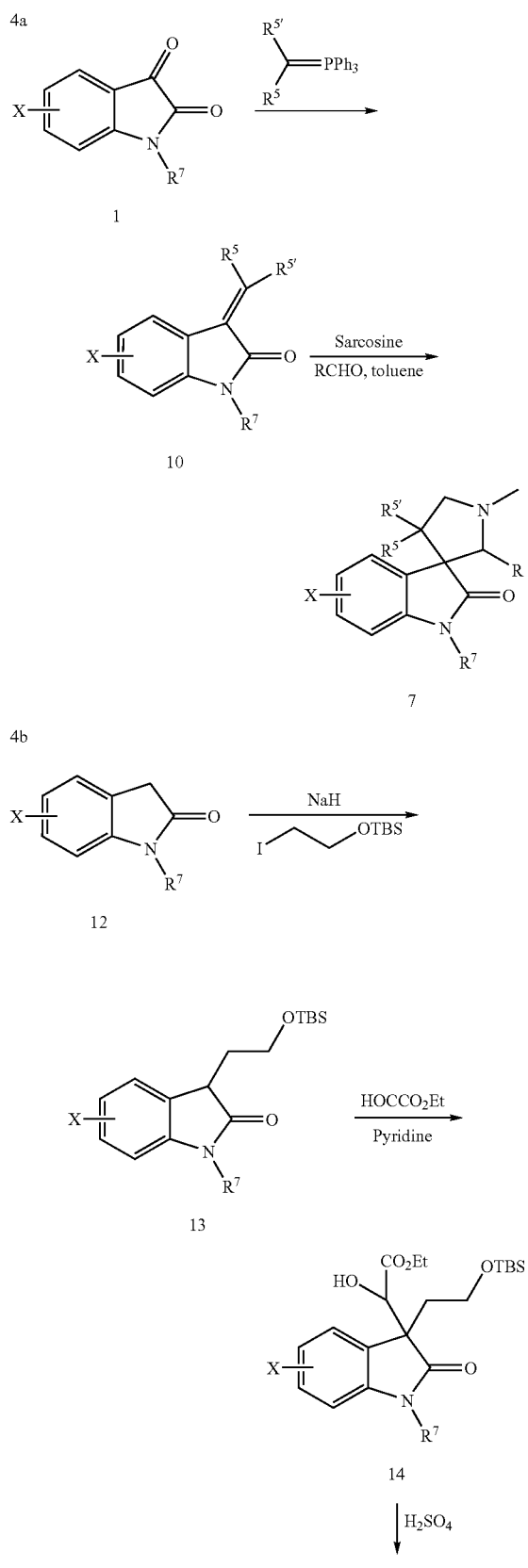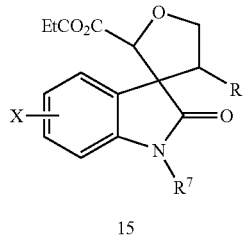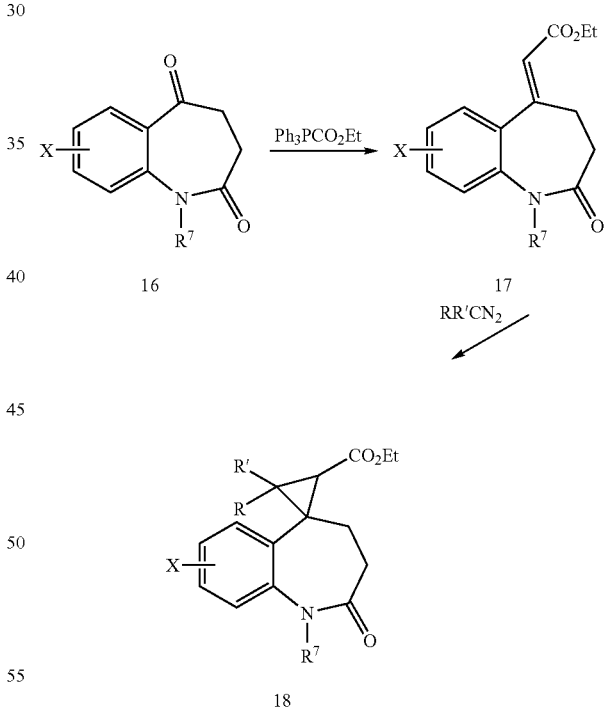

In Scheme 4a, the carbonyl moiety α to the phenyl ring of 3-oxo-lactam 10 is converted to the alkene of 11 via the action of an ylide reagent. The nitrogen-containing heterocycle is prepared by cyclization with an appropriate amine, affording 12.

Scheme 4b provides a route originating with lactam 13, which is alkylated α to the carbonyl moiety, providing protected hydroxyl derivative 14, which also undergoes alkylation at the carbon α to the carbonyl, proving α-hydroxy ester 15. The hydroxy ester is cyclized to 16 in acidic milieu.

Scheme 5 sets forth a route to compounds of the invention in which the six-membered ring system is replaced with a larger system, e.g., a seven-membered ring system.

The carbonyl α to the phenyl group of 16 is converted to the double bond of 17 using an ylide reagent. The cyclopropyl group of 18 is prepared by cyclizing the double bond with an appropriate azide.

In Scheme 6, there is provided a route to compounds of the invention in which the five-membered ring system is replaced with a larger ring. The compounds provided by the route set forth in Scheme 6 also include a cyclopropyl ring at various positions on the larger ring system.

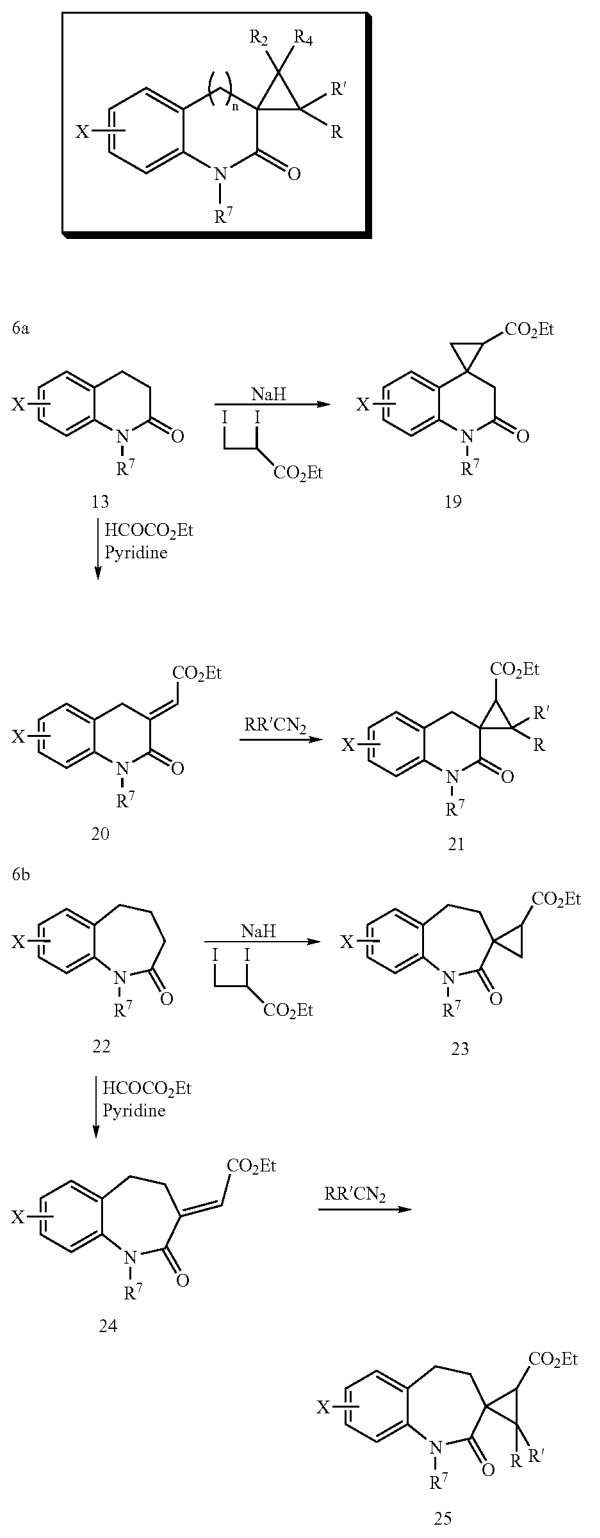

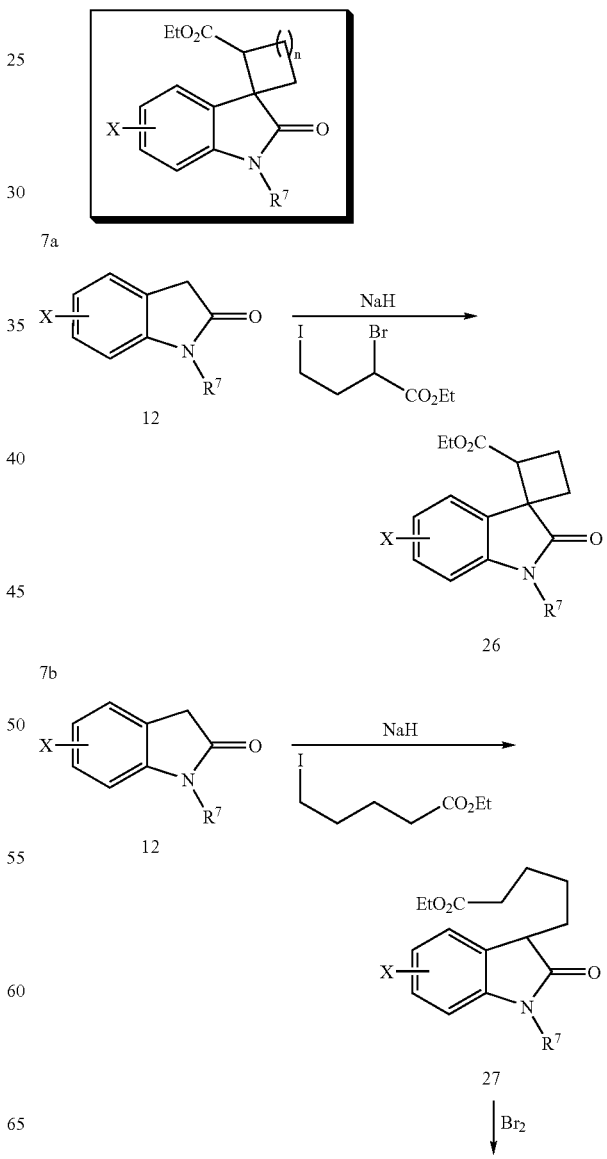

are prepared by alkylating the carbon α to the lactam carbonyl and cyclizing resulting alkene 21 with an appropriate azide to provide 22.

In Scheme 6b, lactam 23 is converted to the spirocyclopropyl derivative 24 by double alkylation accompanied by cyclization of the carbon atom α to the carbonyl of the lactam. As in Scheme 6a, more elaborately substituted cyclopropyl rings are emplaced by alkylation and cyclization of the alkylated product, forming 25 and 26, respectively.

Scheme 7 provides an exemplary route to compounds of the invention in which the cyclopropyl ring is replaced with a larger ring system. Scheme 7a sets forth a route to an oxindole with a spirocyclobutyl ring system. Scheme 7b provides a scheme to an oxindole with a cyclopentyl ring system. Scheme 7b provides a scheme to an oxindole with a cyclohexyl ring system.

In Scheme 6a, lactam 13 is readily derivatized with a spiro-cyclopropyl ring, producing 20 by double alkylation, accompanied by cyclization of the carbon α to the phenyl ring. Cyclopropyl rings that are more extensively substituted

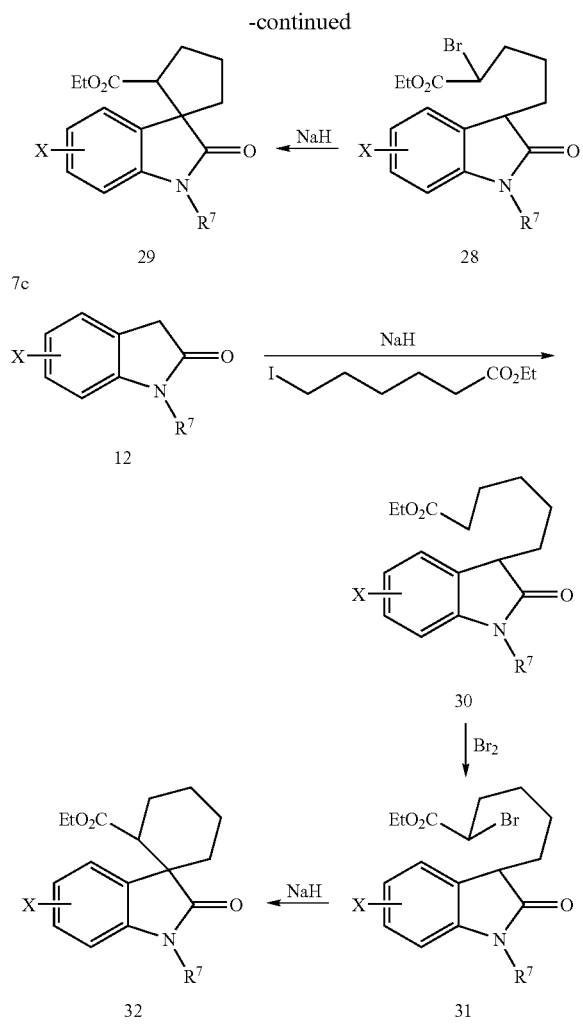

Each of Schemes 7a–7c relies on an alkylation-cyclization pathway. Thus, in each scheme, lactam 13 is alkylated and subsequently cyclized to produce spiro-derivatives 26, 29 and 32.

Figure 1E:
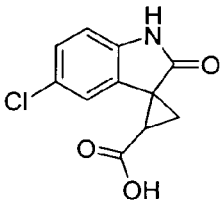
Figure 1E:
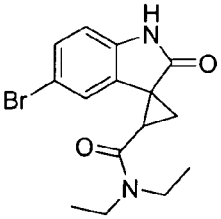
Figure 1E:
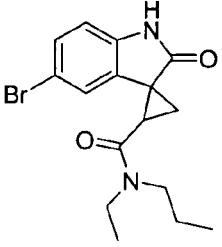
Figure 1E:
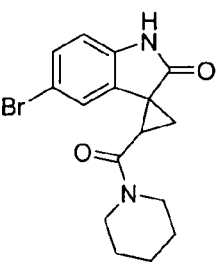
Figure 1F:
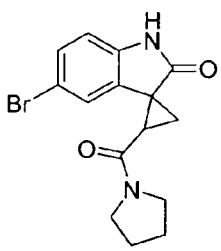
Figure 1F:
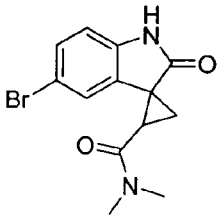
Figure 1F:
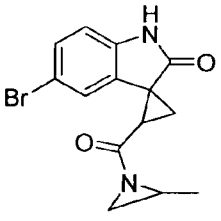
Figure 1F:
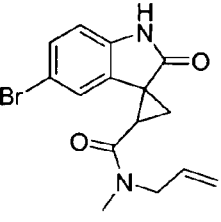
Figure 1F:
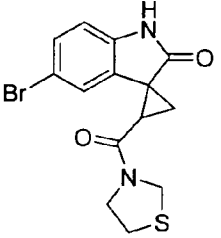
Figure 1I:
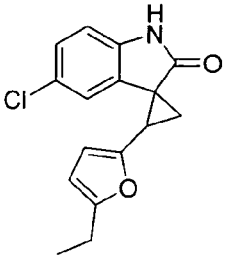
Figure 1I:
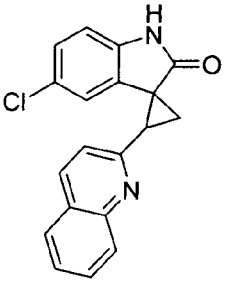
Figure 1I:
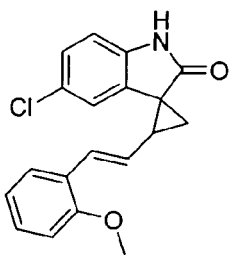
Figure 1I:
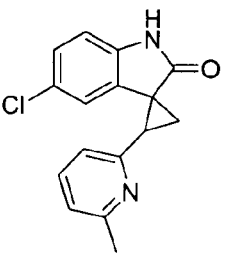
Figure 1K:
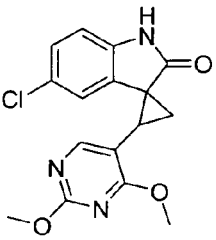
Figure 1K:
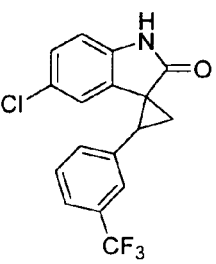
Figure 1K:
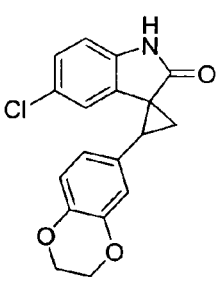
Figure 1K:
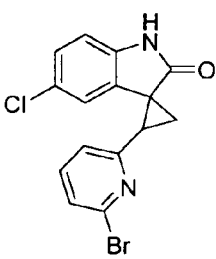
Figure 1L:
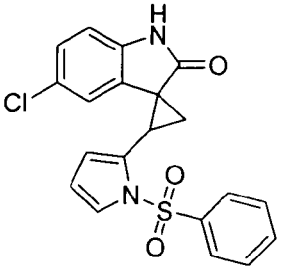
Figure 1L:
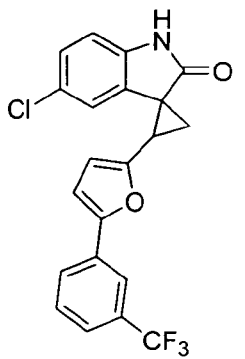
Figure 1L:
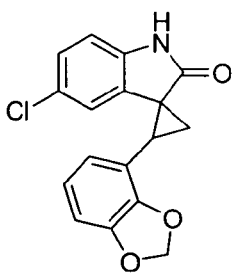
Figure 1L:
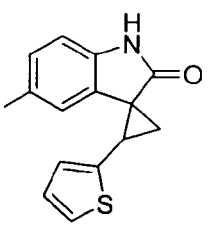
Figure 1N:
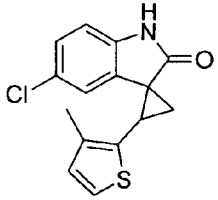
Figure 1N:
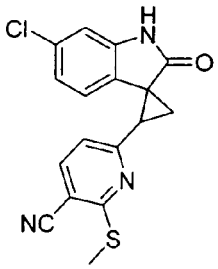
Figure 1N:
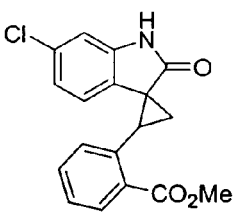
Figure 1N:
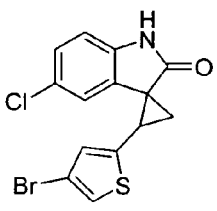
Figure 1N:
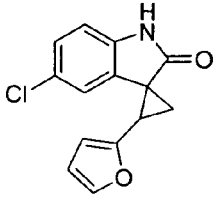
Figure 1R:
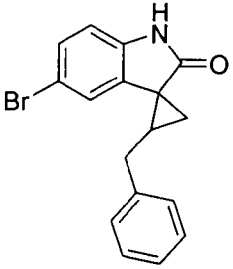
Figure 1R:
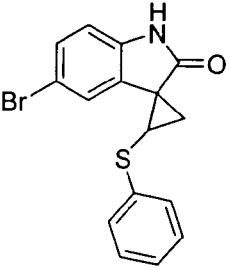
Figure 1R:
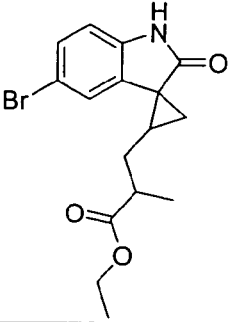
Figure 1R:
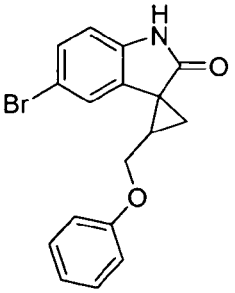
Figure 1T:
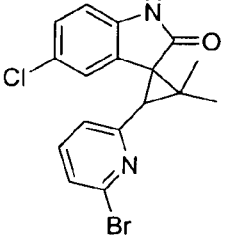
Figure 1T:
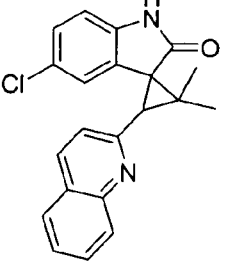
Figure 1T:
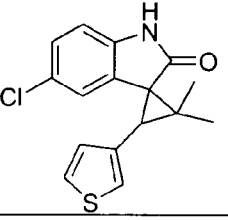
Figure 1T:
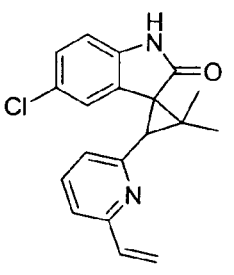
Figure 1T:
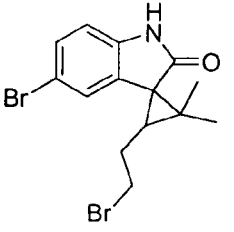
Figure 1U:
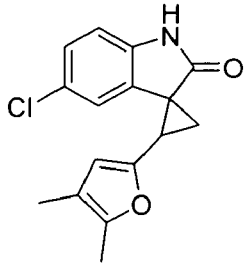

Diversification of the final oxindole product is obtained by making moderations to one or more steps of the above exemplary schemes. For example, the ylide reagent may comprise a wide variety of moieties. Such moieties include, but are not limited to substituted or unsubstituted alkyls, aryls, heteroaryls, or heterocycloalkyls. In addition, the ester provides an ideal handle for additional, e.g., final step diversity. Exemplary compounds produced by such modifications are presented in FIG. 1.

The compounds of the invention are synthesized by either solution phase or solid phase synthesis. The solid support used is not a critical feature of the present invention provided that it is capable of binding to the carboxyl group while remaining substantially inert to the reagents utilized in the synthesis procedure. For example, a starting material can be prepared by attaching an amino-protected precursor via a benzyl ester linkage to a chloromethylated resin or a hydroxymethyl resin or via an amide bond to a benzhydrylamine (BHA) resin or p-methylbenzhydrylamine (MBHA) resin. Materials suitable for us as solid supports are well known to those of skill in the art and include, but are not limited to, the following: halomethyl resins, such as chloromethyl resin or bromomethyl resin; hydroxymethyl resins; phenol resins, such as 4-(α-[2,4-dimethoxyphenyl]-Fmoc-aminomethyl)phenoxy resin; tert-alkyloxycarbonyl-hydrazidated resins, and the like. Such resins are commercially available and methods for their preparation are known by those of ordinary skill in the art.

The compounds of the present invention can be isolated and purified from the reaction mixture by means of purification strategies well known to those of skill in the art. For example, the compounds may be purified using known chromatographic procedures such as reverse phase HPLC, gel permeation, ion exchange, size exclusion, affinity, partition, or countercurrent distribution.

Pharmaceutical Formulations

The compounds of the present invention can be prepared and administered in a wide variety of oral, parenteral and topical dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. Accordingly, the present invention also provides pharmaceutical compositions comprising a pharmaceutically acceptable carrier or excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The dose administered to a patient, in the context of the present invention should be sufficient to provide a beneficial therapeutic response in the patient over time. The dose is determined by the efficacy of the particular compound employed and the condition of the patient, as well as the body weight or surface area of the patient to be treated. The size of the dose also is determined by the existence, nature, and extent of any adverse side effects that accompany the administration of a particular compound in a particular patient.

The compound can also be introduced into an animal cell, preferably a mammalian cell, via a microparticles and liposomes and liposome derivatives such as immunoliposomes. The term "liposome" refers to vesicles comprised of one or more concentrically ordered lipid bilayers, which encapsulate an aqueous phase. The aqueous phase typically contains the compound to be delivered to the cell.

The liposome fuses with the plasma membrane, thereby releasing the drug into the cytosol. Alternatively, the liposome is phagocytosed or taken up by the cell in a transport vesicle. Once in the endosome or phagosome, the liposome either degrades or fuses with the membrane of the transport vesicle and releases its contents.

In current methods of drug delivery via liposomes, the liposome ultimately becomes permeable and releases the encapsulated compound at the target tissue or cell. For systemic or tissue specific delivery, this can be accomplished, for example, in a passive manner wherein the liposome bilayer degrades over time through the action of various agents in the body. Alternatively, active drug release involves using an agent to induce a permeability change in the liposome vesicle. Liposome membranes can be constructed so that they become destabilized when the environment becomes acidic near the liposome membrane (see, e.g., *PNAS* 84:7851 (1987); *Biochemistry* 28:908 (1989)). When liposomes are endocytosed by a target cell, for example, they become destabilized and release their contents. This destabilization is termed fusogenesis. Dioleoylphosphatidyl-ethanolamine (DOPE) is the basis of many "fusogenic" systems.

Such liposomes typically comprise a compound of choice and a lipid component, e.g., a neutral and/or cationic lipid, optionally including a receptor-recognition molecule such as an antibody that binds to a predetermined cell surface receptor or ligand (e.g., an antigen). A variety of methods are available for preparing liposomes as described in, e.g., Szoka et al., *Ann. Rev. Biophys. Bioeng.* 9:467 (1980), U.S. Pat. Nos. 4,186,183, 4,217,344, 4,235,871, 4,261,975, 4,485,054, 4,501,728, 4,774,085, 4,837,028, 4,235,871, 4,261,975, 4,485,054, 4,501,728, 4,774,085, 4,837,028, 4,946,787, PCT Publication No. WO 91\17424, Deamer & Bangham, *Biochim. Biophys. Acta* 443:629–634 (1976); Fraley, et al., *PNAS* 76:3348–3352 (1979); Hope et al., *Biochim. Biophys. Acta* 812:55–65 (1985); Mayer et al., *Biochim. Biophys. Acta* 858:161–168 (1986); Williams et al., *PNAS* 85:242–246 (1988); *Liposomes* (Ostro (ed.), 1983, Chapter 1); Hope et al., *Chem. Phys. Lip.* 40:89 (1986); Gregoriadis, *Liposome Technology* (1984) and Lasic, *Liposomes: from Physics to Applications* (1993)). Suitable methods include, for example, sonication, extrusion, high pressure/homogenization, microfluidization, detergent dialysis, calcium-induced fusion of small liposome vesicles and ether-fusion methods, all of which are well known in the art.

In certain embodiments of the present invention, it is desirable to target the liposomes of the invention using targeting moieties that are specific to a particular cell type, tissue, and the like. Targeting of liposomes using a variety of targeting moieties (e.g., ligands, receptors, and monoclonal antibodies) has been previously described (see, e.g., U.S. Pat. Nos. 4,957,773 and 4,603,044).

Standard methods for coupling targeting agents to liposomes can be used. These methods generally involve incorporation into liposomes lipid components, e.g., phosphatidylethanolamine, which can be activated for attachment of targeting agents, or derivatized lipophilic compounds, such as lipid-derivatized bleomycin. Antibody targeted liposomes can be constructed using, for instance, liposomes which incorporate protein A (see Renneisen et al., *J. Biol. Chem.*, 265:16337–16342 (1990) and Leonetti et al., *PNAS* 87:2448–2451 (1990)).

In determining the effective amount of the compound to be administered in the treatment or prophylaxis of conditions owing to HIV infection, the physician evaluates circulating plasma levels of the compound; compound toxicities, progression of the disease, and the production of viral resistance to the compound.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The quantity of active component in a unit dose preparation may be varied or adjusted from 0.1 mg to 10 g, more typically 1.0 mg to 1 g, most typically 10 mg to 500 mg, according to the particular application and the potency of the active component. The composition can, if desired, also contain other compatible therapeutic or diagnostic agents. Administration can be accomplished via single or divided doses.

The Methods

The present invention also provides methods for treating or ameliorating HIV disease and related diseases. The method includes administering a therapeutically effective dosage of at least one compound of the invention to a subject suffering from HIV disease or HIV-related diseases. The invention also provides a method of combination therapy in which one or more compound of the invention is administered in combination with one or more other compound having activity against HIV disease or HIV-related disease. Furthermore, the invention provides methods for inhibiting drug resistant HIV mutants.

The high replication rate of HIV leads to genetic variants (mutants), especially when selective pressure is introduced in the form of drug treatment. The mutants frequently display resistance to anti-viral agents previously administered to the patient. Switching agents or using combination therapies may decrease or delay resistance, but because viral replication is not completely suppressed in single drug treatment or even with a two-drug combination, drug-resistant viral strains ultimately emerge. Triple drug combinations employing one (or two) nucleoside analogs and two (or one) non-nucleoside inhibitor (NNI) targeting RT provide a very promising therapy to overcome the drug resistance problem. RT mutant strains resistant to such a triple action drug combination would most likely not be able to function.

Dozens of mutant strains have been characterized as resistant to NNI compounds, including L1001, K103N, V106A, E138K, Y181C and Y188H. In particular, the Y181C and K103N mutants may be the most difficult to treat, because they are resistant to most of the NNI compounds that have been examined.

Dosage levels of approximately 0.02 to approximately 10.0 grams of a compound of the invention per day are useful in the treatment or prevention of retroviral infection, such as HIV infection, AIDS or AIDS-related complex (ARC), with oral doses 2 to 5 times higher. For example, HIV infection can be treated by administration of from about 0.1 to about 100 milligrams of compound per kilogram of body weight from one to four times per day. In one embodiment, dosages of about 100 to about 400 milligrams of compound are administered orally every six hours to a subject. The specific dosage level and frequency for any particular subject is varied and will depend upon a variety of factors, including the activity of the specific compound the metabolic stability and length of action of that compound, the age, body weight, general health, sex, and diet of the subject, mode of administration, rate of excretion, drug combination, and severity of the particular condition.

Combination Therapies

The present invention also provides methods for treating or ameliorating HIV disease and related diseases. The method includes administering a therapeutically effective dosage of at least one compound of the invention to a subject suffering from HIV disease or HIV-related diseases. The invention also provides a method of combination therapy in which one or more compound of the invention is administered in combination with one or more other compound having activity against HIV disease or HIV-related disease.

Dosage levels of approximately 0.02 to approximately 10.0 grams of a compound of the invention per day are useful in the treatment or prevention of retroviral infection, such as HIV infection, AIDS or AIDS-related complex (ARC), with oral doses 2 to 5 times higher. For example, HIV infection can be treated by administration of from about 0.1 to about 100 milligrams of compound per kilogram of body weight from one to four times per day. In one embodiment, dosages of about 100 to about 400 milligrams of compound are administered orally every six hours to a subject. The specific dosage level and frequency for any particular subject is varied and will depend upon a variety of factors, including the activity of the specific compound the metabolic stability and length of action of that compound, the age, body weight, general health, sex, and diet of the subject, mode of administration, rate of excretion, drug combination, and severity of the particular condition.

The invention provides methods for inhibiting the replication of drug resistant HIV mutants. The high replication rate of HIV leads to genetic variants (mutants), especially when selective pressure is introduced in the form of drug treatment. The mutants frequently display resistance to anti-viral agents previously administered to the patient. Switching agents or using combination therapies may decrease or delay resistance, but because viral replication is not completely suppressed in single drug treatment or even with a two-drug combination, drug-resistant viral strains ultimately emerge. Triple drug combinations employing one (or two) nucleoside analogs and two (or one) non-nucleoside inhibitor (NNI) targeting RT provide a very promising therapy to overcome the drug resistance problem. RT mutant strains resistant to such a triple action drug combination would most likely not be able to function.

Dozens of mutant strains have been characterized as resistant to NNI compounds, including L1001, K103N, V106A, E138K, Y181C and Y188H. In particular, the Y181C and K103N mutants may be the most difficult to treat, because they are resistant to most of the NNI compounds that have been examined.

Assays for Modulators of Reverse Transcriptase

Modulation of a reverse transcriptase, and corresponding modulation of HIV and viral infection, preferably inhibition, can be assessed using a variety of in vitro and in vivo assays, including cell-based models. Such assays can be used to test for inhibitors and activators of reverse transcriptase, and, consequently, inhibitors and activators of HIV infection and HIV-associated diseases. Such modulators of reverse transcriptase are useful for treating disorders related to HIV infection, as described herein. Modulators of reverse transcriptase are tested using either recombinant, chemically synthesized or naturally occurring reverse transcriptase.

Preferred modulators of the invention are those that act to decrease reverse transcriptase activity at the protein level. Preferred modulators also include those that decrease expression of reverse transcriptase at the nucleic acid level, e.g., inhibitors of the reverse transcriptase promoter, compounds that increase chromosome accessibility of the reverse transcriptase gene, compounds that decrease reverse transcriptase RNA stability and processing, and compounds that decrease reverse transcriptase RNA levels in the cytoplasm or nucleus.

Measurement of HIV infection modulation with a reverse transcriptase inhibitor can be performed using a variety of assays, in vitro, in vivo, and ex vivo, as described herein. A suitable physical, chemical or phenotypic change that affects activity, e.g., enzymatic activity, cell proliferation (e.g., CD4+ lymphocyte proliferation), HIV replication, expression of HIV proteins, or ligand or substrate binding can be used to assess the influence of a test compound on the polypeptide of this invention. When the functional effects are determined using intact cells or animals, one can also measure a variety of effects, such as, viral RNA levels or viral titers in serum, ligand binding, transcriptional changes to both known and uncharacterized genetic markers (e.g., northern blots), changes in cell metabolism, changes related to cellular proliferation, viral marker expression, DNA synthesis, marker and dye dilution assays (e.g., GFP and cell tracker assays), etc.

In Vitro Assays

Assays to identify compounds with reverse transcriptase modulating activity can be performed in vitro. As described below, the assay can be either solid state or soluble. The protein may be bound to a solid support, either covalently or non-covalently. Often, the in vitro assays of the invention are substrate or ligand binding or affinity assays, either non-competitive or competitive. Other in vitro assays include measuring changes in spectroscopic (e.g., fluorescence, absorbance, refractive index), hydrodynamic (e.g., shape), chromatographic, or solubility properties for the protein.

In one embodiment, a high throughput-binding assay is performed in which the reverse transcriptase or a fragment thereof is contacted with a potential modulator and incubated for a suitable amount of time. In one embodiment, the potential modulator is bound to a solid support, and the reverse transcriptase is added. In another embodiment, the reverse transcriptase is bound to a solid support. A wide variety of assays can be used to identify reverse transcriptase-modulator binding, including labeled protein-protein binding assays, electrophoretic mobility shifts, immunoassays, enzymatic assays such as kinase assays, and the like. In some cases, the binding of the candidate modulator is determined through the use of competitive binding assays, where interference with binding of a known ligand or substrate is measured in the presence of a potential modulator. Either the modulator or the known ligand or substrate is bound first, and then the competitor is added. After the reverse transcriptase is washed, interference with binding, either of the potential modulator or of the known ligand or substrate, is determined. Often, either the potential modulator or the known ligand or substrate is labeled.

Cell-Based In Vivo Assays

In another embodiment, reverse transcriptase is expressed in a cell, and functional, e.g., physical and chemical or phenotypic, changes are assayed to identify modulators of reverse transcriptase and modulators of HIV replication and HIV infected cells. Cells expressing reverse transcriptase can also be used in binding assays and enzymatic assays. Any suitable functional effect can be measured, as described herein. For example, cellular morphology (e.g., cell volume, nuclear volume, cell perimeter, and nuclear perimeter), ligand binding, lymphocyte proliferation, apoptosis, viral marker expression, GFP positivity and dye dilution assays (e.g., cell tracker assays with dyes that bind to cell membranes), DNA synthesis assays (e.g., $^3$H-thymidine and fluorescent DNA-binding dyes such as BrdU or Hoechst dye with FACS analysis), are all suitable assays to identify potential modulators using a cell based system. Suitable cells for such cell based assays include both primary cells such as PBMCs, lymphocytes (e.g., CD4+), neutrophils, polymorphonuclear leukocytes, and other phagocytic cells and cell lines, e.g., Jurkat cells, BJAB cells, etc. The reverse transcriptase can be naturally occurring or recombinant.

Cellular reverse transcriptase RNA and polypeptide levels can be determined by measuring the level of protein or mRNA. The level of reverse transcriptase or proteins related to reverse transcriptase are measured using immunoassays such as western blotting, ELISA and the like with an antibody that selectively binds to the reverse transcriptase polypeptide or a fragment thereof. For measurement of mRNA, amplification, e.g., using PCR, LCR, or hybridization assays, e.g., northern hybridization, RNAse protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, reverse transcriptase expression can be measured using a reporter gene system, e.g., utilizing a fusion protein or a gene linked to a reverse transcriptase promoter. Such a system can be devised using a reverse transcriptase protein promoter operably linked to a reporter gene such as chloramphenicol acetyltransferase, firefly luciferase, bacterial luciferase, β-galactosidase and alkaline phosphatase. Furthermore, the protein of interest can be used as an indirect reporter via attachment to a second reporter such as red or green fluorescent protein (see, e.g., Mistili & Spector, *Nature Biotechnology* 15:961–964 (1997)). The reporter construct is typically transfected into a cell. After treatment with a potential modulator, the amount of reporter gene transcription, translation, or activity is measured according to standard techniques known to those of skill in the art.

Animal Models

Animal models of HIV infection also find use in screening for modulators of reverse transcriptase. Similarly, transgenic animal technology including gene knockout technology, for example as a result of homologous recombination with an appropriate gene targeting vector, or gene overexpression, will result in the absence or increased expression of the reverse transcriptase. The same technology can also be applied to make knockout cells. When desired, tissue-specific expression or knockout of the reverse transcriptase protein may be necessary.

Knock-out cells and transgenic mice can be made by insertion of a marker gene or other heterologous gene into an endogenous reverse transcriptase gene site in the mouse genome via homologous recombination. Such mice can also be made by substituting an endogenous reverse transcriptase with a mutated version of the reverse transcriptase gene by mutating an endogenous reverse transcriptase, e.g., by exposure to carcinogens.

A DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi et al., *Science* 244:1288 (1989)). Chimeric targeted mice can be derived according to Hogan et al., *Manipulating the Mouse Embryo: A Laboratory Manual*, Cold Spring Harbor Laboratory (1988) and *Teratocarcinomas and Embryonic Stem Cells: A Practical Approach*, Robertson, ed., IRL Press, Washington, D.C., (1987).

Solid State and Soluble High Throughput Assays

In one preferred embodiment, high throughput screening methods involve providing a combinatorial small organic molecule or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991) and Houghton et al., *Nature* 354:84–88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309–314 (1996) and PCT/US96/10287), carbohydrate libraries (see, e.g., Liang et al., *Science*, 274: 1520–1522 (1996) and U.S. Pat. No. 5,593,853), small organic molecule libraries (see, e.g., benzodiazepines, Baum C&EN, Jan 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

In one embodiment the invention provides soluble assays using a reverse transcriptase protein, or a cell or tissue expressing a reverse transcriptase, either naturally occurring or recombinant. In another embodiment, the invention provides solid phase based in vitro assays in a high throughput format, where the reverse transcriptase is attached to a solid phase. Any one of the assays described herein can be adapted for high throughput screening.

In the high throughput assays of the invention, either soluble or solid state, it is possible to screen up to several thousand different modulators or ligands in a single day. This methodology can be used for reverse transcriptase in vitro, or for cell-based or membrane-based assays comprising a reverse transcriptase protein. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (e.g., 96) modulators. If 1536 well plates are used, then a single plate can easily assay from about 100- about 1500 different compounds. It is possible to assay many plates per day; assay screens for up to about 6,000, 20,000, 50,000, or more than 100,000 different compounds are possible using the integrated systems of the invention.

For a solid state reaction, the protein of interest or a fragment thereof, e.g., an extracellular domain, or a cell or membrane comprising the protein of interest or a fragment thereof as part of a fusion protein can be bound to the solid state component, directly or indirectly, via covalent or non covalent linkage. A tag for covalent or non-covalent binding can be any of a variety of components. In general, a molecule that binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody that recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I*(1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent that fixes a chemical group to the surface that is reactive with a portion of the tag binder. For example, groups that are suitable for attachment to a longer chain portion include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149–2154 (1963) (describing solid phase synthesis of, e.g., peptides); Geysen et al., *J. Immun. Meth.* 102:259–274 (1987) (describing synthesis of solid phase components on pins); Frank & Doring, *Tetrahedron* 44:60316040 (1988) (describing synthesis of various peptide sequences on cellulose disks); Fodor et al., *Science*, 251:767–777 (1991); Sheldon et al., *Clinical Chemistry* 39(4):718–719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

EXAMPLES

The following examples are offered to illustrate, but not to limit the claimed invention.

Example 1

1.1 Preparation of (5-bromo-1,2-dihydro-2-oxo-3H-indol-3-ylidene), ethyl ester

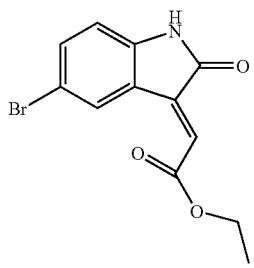

A solution containing 5-bromoisatin (226 mg, 1 mmol) and (carbethoxymethyl)-triphenylphosphorane (383 mg, 1.1 mmol) in toluene (20 mL) was stirred at 80° C. under argon for 16 hours. The reaction mixture was concentrated to dryness in vacuo and the residue was chromatographed using hexane and ethyl acetate (v/v 4:1) as eluent. The title compound was isolated (220 mg, 75%) as orange crystals. MS: m/z 296 [M+1]$^+$. $^1$H 1 NMR (DMSO-d$_6$): δ 8.51 (d, 1H), 7.53 (m, 1H), 6.84 (d, J=8 Hz, 1H), 6.57 (s, 1H), 4.24 (m, 2H), 1.29 (t, 3H).

1.2 Preparation of 5-Bromo-1,2-dihydro-2-oxo-3H-indol-3-ylidene)acetonitrile

The title compound was prepared using a method analogous to that set forth above. MS m/z 249.0 [M+1]$^+$.

Example 2

Preparation of 5-chloro-1,3-dihydro-3-(2-pyridinyl-methylene)-2H-indol-2-one

A 5 mL of ethanol solution containing 5-chlorooxindole (167 mg, 1 mmol), 2-pyridine-carboxaldehyde (129 mg, 1.2 mmol) and 3 drops of piperidine was stirred at 80° C. for 6 hours. After cooling the solution to 5° C., yellow precipitate was obtained (200 mg, 78%). MS: m/z 257 [M+1]$^+$.

Example 3

Preparation of spiro[cyclopropane-1,3'-[3H]indole]-2-carboxylic acid-1',2'-dihydro-2'-oxo-5'-bromo, ethyl ester

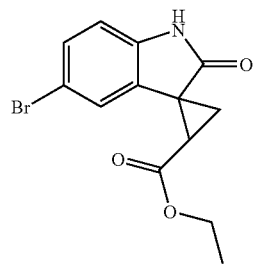

An excess of an ethereal diazomethane solution was added portion-wise from a syringe to a suspension of 5-bromo-1,2-dihydro-2-oxo-3H-indol-3-ylidene, ethyl ester (30 mg, 0.1 mmol), prepared as set forth in Example 1, in dry ether (30 mL). The suspension was stirred at 0° C. for 2 hours. Excess diazomethane was quenched with two drops of acetic acid. The reaction mixture was concentrated to dryness in vacuo and the residue was dissolved in toluene (20 mL). The resulting solution was heated to reflux for 6 hours. Following removal of the solvents, the solid residue was chromatographed using hexane and ethyl acetate (v/v 1:1) as eluent. The title compound was isolated in 50% yield (15 mg). MS: m/z 310 [M+1]$^+$.

$^1$H NMR (CCl$_3$D): δ 7.89 (br, 1H), 7.52 (br, 1H), 7.35 (m, 1H), 6.82 (m, 1H), 4.12 (t, 2H), 2.72 (m, 1H), 2.16 (m, 1H), 2.04 (m, 1H), 1.25 (m, 3H).

Example 4

Preparation of spiro[cyclopropane-1,3'-[3H]indole]-2-carboxylic acid-1',2'-dihydro-2'-oxo-5'-[2"-furfuryl], ethyl ester

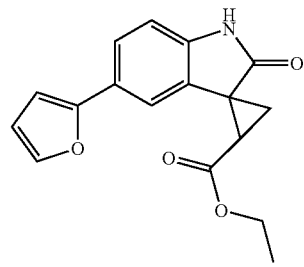

A solution of spiro[cyclopropane-1,3'-[3H]indole]-2-carboxylic acid-1',2'-dihydro-2'-oxo-5'-bromo, ethyl ester (22.6 mg, 0.1 mmol), prepared as in Example 3, 2-furanyltributylstannane (43 mg, 0.12 mmol) and dichlorobis(triphenylphosphine)-palladium (2 mg, 1% weight) in DMF (10 mL) was heated to 90° C. under argon for 16 hours. The reaction mixture was concentrated to dryness in vacuo and the residue was chromatographed using hexane and ethyl acetate (v/v 2:1) as eluent. The title compound was isolated in 84% yield 25 mg as a white solid. MS: m/z 298 [M+1]$^+$.

Example 5

Preparation of spiro[cyclopropane-1,3'-[3H]indole]-2-carboxylic acid, 1',2'-dihydro-2'-oxo-5'-bromo

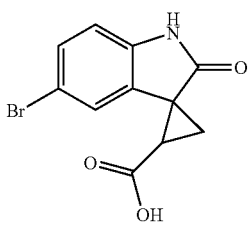

A solution containing spiro[cyclopropane-1,3'-[3H]indole]-2-carboxylic acid, 1',2'-dihydro-2'-oxo-5'-bromo, ethyl ester (31 mg, 0.1 mmol), prepared as set forth in Example 3, and 0.3 mL of NaOH (1N) in 5 mL of MeOH was stirred at 40° C. under argon for 16 hours after which the reaction mixture was acidified using HCl (1N). The resulting precipitate yielded 20 mg (71%) of the title compound. MS: m/z 282 [M+1]$^+$.

Example 6

Preparation of spiro[cyclopropane-1,3'-[3H]indole]-2-carboxylic acid-1',2'-dihydro-2'-oxo-5'-bromo, N,N-diethyl amide

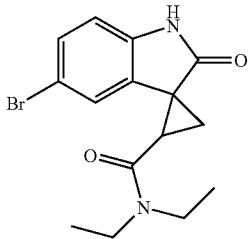

A solution containing spiro[cyclopropane-1,3'-[3H]indole]-2-carboxylic acid-1',2'-dihydro-2'-oxo-5'-bromo (28 mg, 0.1 mmol) and EDCI (38 mg, 0.2 mmol) in 10 mL of CH$_2$Cl$_2$ was stirred at 0° C. for one half hour. To the solution, N,N-diethylamine (0.3 mmol) was added. The solution was warmed to room temperature and stirred for 16 hours. Upon removal of the solvents, the solid residue was chromatographed using hexane and ethyl acetate (v/v 1:2) as eluent. The chromatographed material gave the title compound in 87% yield (29 mg). MS: m/z 337 [M+1]$^+$.

Example 7

Preparation of 5'-chloro-2-(2-pyridinyl)-spiro[cyclopropane-1,3'-[3H]indol]-2'(1'H)-one

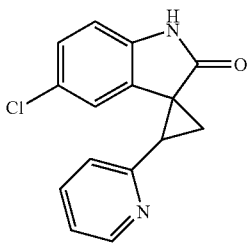

An excess of an ethereal diazomethane solution was added portion wise from a syringe to a suspension of 5-bromo-1,3-dihydro-3-(2-pyridinylmethylene)-2H-indol-2-one, prepared as in Example 2, (26 mg, 0,1 mmol) and Rh$_2$(OAc)$_4$ (1 mg) in 30 mL of dry ether. The suspension was stirred at 0° C. for 16 hours. Excess diazomethane was quenched with two drops of acetic acid. The reaction mixture was concentrated to dryness in vacuo. The solid residue was chromatographed using hexane and ethyl acetate (v/v 1:1) as eluent. The chromatographed material gave the title compound in 50% yield (13 mg). MS: m/z 271 [M+1]$^+$. $^1$H NMR (DMSO-d$_6$): δ 8.76 (s, 1H), 8.64 (m, 1H), 7.62 (m, 1H), 7.25 (m, 1H), 7.20 (m, 1H), 7.05 (m, 1H), 6.82 (d, 1H), 6.79(d, 1H), 3.36 (t, 1H), 2.65 (m, 1H), 2.25 (m, 1H).

Example 8

Preparation of 5'-bromo-2-cyano-spiro[cyclopropane-1,3'-[3H]indol]-2'(1'H)-one

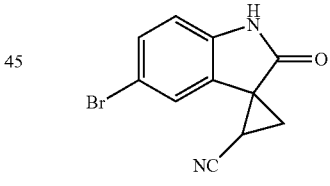

An excess of an ethereal diazomethane solution was added portion-wise from a syringe to a suspension of 5-bromo-1,2-dihydro-2-oxo-3H-indol-3-ylidene-acetonitrile (30 mg, 0.1 mmol), prepared as in Example 1, in dry ether (30 mL). The suspension was stirred at 0° C. for 2 hours. Excess diazomethane was quenched with two drops of acetic acid. The reaction mixture was concentrated to dryness in vacuo. The residue was dissolved in toluene (20 mL) and the resulting solution was heated to reflux for 6 hours. Upon removal of the solvents, the solid residue was chromatographed using hexane and ethyl acetate (v/v 1:1) as eluent, providing the title compound in 50% yield (15 mg). MS: m/z 263.2 [M+1]$^+$. $^1$H NMR (CCl$_3$D): δ 9.06 (br, 1H), 7.45 (m, 1H), 7.30 (br, 1H), 6.87(m, 1H), 2.50 (m, 1H), 2.16 (m, 1H), 1.93 (m, 1H).

Example 9

Preparation of 5'-Bromo-2-(tetrazole-5-yl)-spiro[cyclopropane-1,3'-[3H]indol]-2'(1'H)-one

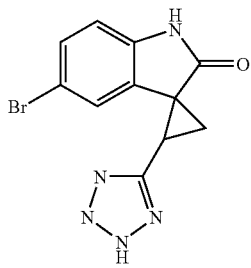

A suspension containing 5'-bromo-2-cyano-spiro[cyclopropane-1,3'-[3H]indol]-2'(1'H)-one (263 mg, 1 mmol) and trimethyltin azide(384 mg, 2 mmol) in xylene (20 mL) was stirred and heated to reflux for 16 hours. After cooling the solution to 5° C., a white precipitate was obtained that gave 210 mg (yield: 69%) of the title compound. MS: m/z 206 [M+1]$^+$; $^1$H NMR (DMSO-d$_6$): δ 10.7 (br, 1H), 7.14 (m, 1H), 7.0 (m, 2H), 6.70 (d, 1H), 2.90 (m, 1H), 2.24 (m, 1H). 1.98 (m, 1H).

Example 10

Preparation of 5'-bromo-2-(3-methyltetrazole-5-yl)-spiro[cyclopropane-1,3'-[3H]indol]-2'(1'H)-one

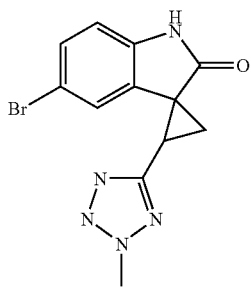

A suspension containing 5'-bromo-2-(tetrazole-5-yl)-spiro[cyclopropane-1,3'-[3H]indol]-2'(1'H)-one (153 mg, 0.5 mmol), iodomethane (85 mg, 0.6 mmol) and sodium hydroxide (20 mg, 0.5 mmol) in 5 mL of DMF was stirred at room temperature for 16 hours. The reaction mixture was concentrated to dryness in vacuo. The solid residue was chromatographed using hexane and ethyl acetate (v/v 1:1) as eluent. The chromatographed material gave the title compound in 34% yield (55 mg). MS m/z 320 [M+1]$^+$. $^1$H NMR (CDCl$_3$): δ 8.52 (s, 1H), 7.27 (m, 1H), 7.04 (br, 1H), 6.80 (m, 1H), 4.34 (s, 3H), 3.35 (t, 1H), 2.48 (m, 1H), 2.05 (m, 1H).

Example 11

Preparation of 5'-chloro-2-(6-phenyl-2-pyridinyl)-spiro[cyclopropane-1,3'-[3H]indol]-2'(1'H)-one

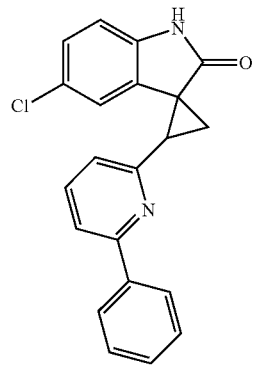

A suspension containing 5'-chloro-2-(5-bromopyridyl-2-yl)-spiro[cyclopropane-1,3'-[3H]indol]-2'(1'H)-one (34 mg, 0.1 mmol), tributylphenyl stannane (40 mg, 0.11 mmol) and tetrakis(triphenylphosphine)palladium (6 mg, 0.005 mmol) in toluene (10 mL) was heated to reflux for 16 hours. The reaction mixture was concentrated to dryness in vacuo. The solid residue was chromatographed using hexane and ethyl acetate (v/v 1:1) as eluent. The chromatographed material gave the title compound in 57% yield (20 mg). MS: m/z 347 [M+1]$^+$. $^1$H NMR (CDCl$_3$): δ 8.28 (m, 2H), 8.06 (s, 1H), 7.64 (m, 2H), 7.51 (m, 2H), 7.40 (m, 1H), 7.18 (m, 1H), 7.02 (m, 2H), 6.75 (d, 1H), 3.48 (1H), 2.86 (m, 1H), 2.29 (m, 1H).

Example 12

Preparation of 5'-bromo-2-butyl-spiro[cyclopropane-1,3'-[3H]indol]-2'(1'H)-one

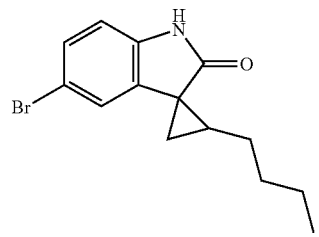

A solution containing 1-hexene (10 equiv.) and 1 mol % of rhodium (II) acetate in dry dichloromethane (10 mL) was degasified under an argon atmosphere. To this reaction mixture, a solution of 5-bromo-3-diazo-oxindole (1 equiv.) (J. Am. Chem. Soc. 1958, 80, 2257–2263) was added dropwise slowly over 1 h under an argon atmosphere at room temperature. The reaction mixture was stirred for 16 hours at room temperature, and concentrated to dryness in vacuo. The solid residue was chromatographed using hexane and ethyl acetate (v/v 1:1) as eluent. The chromatographed material gave the title compound in 70% yield. MS: m/z 294.3 [M+1]$^+$. $^1$H NMR (CCl$_3$D): δ 8.32 (br, 1H), 7.25 (d, 1H), 6.89 (d, 1H), 6.78 (d, 1H), 1.89 (m, 2H), 1.65 (m, 1H), 1.51 (m, 2H), 1.18–1.31 (m, 4H), 0.79 (t, 3H).

Example 13

Preparation of spiro[cyclopropane-1,3'-[3H]indole]-2-carboxylic acid-1',2'-dihydro-2'-oxo-5'-bromo-3,3-dimethyl, ethyl ester

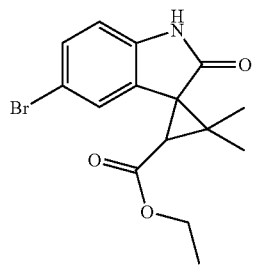

A solution of 5-bromo-1,2-dihydro-2-oxo-3H-indol-3-ylidene), ethyl ester (25 mg, 0.1 mmol) in dry THF (20 mL) was cooled to −78° C. To the solution, a 1M THF solution of 2-propylidene-triphenylphosphorane (2 mL) was added dropwise. After the addition was complete, the solution was warmed to room temperature and stirred for 16 hours. The solvent was removed and the residue was chromatographed using hexane and ethyl acetate (v/v 1:1) as the eluent, providing the title compound in 30% yield (10 mg). $^1$H NMR (500 MHz, CDCl$_3$): δ 7.83 (br, 1H), 7.76 (s, 1H), 7.33 (d, J=8.2 Hz, 1H), 6.78 (d, J=8.2 Hz, 1H), 4.15 (t, J=7.3 Hz, 2H), 2.78 (s, 1H), 1.57 (s, 3H), 1.56 (s, 3H), 1.26 (t, J=7.3 Hz, 3H). MS: m/z 338 [M+1]$^+$.

Example 14

Preparation of spiro[cyclopropane-1,3'-[3H]indole]-2-carboxylic acid-1',2'-dihydro-2'-oxo-5'-chloro, ethyl ester The title compound was prepared in 45% (overall yield) as a white solid following a procedure analogous to that used to prepare spiro[cyclopropane-1,3'-[3H]indole]-2-carboxylic acid-1',2'-dihydro-2'-oxo-5'-bromo, ethyl ester. MS: m/z 266 [M+1]$^+$.

Example 15

Preparation of spiro[cyclopropane-1,3'-[3H]indole]-2-carboxylic acid-1',2'-dihydro-2'-oxo-5'-fluoro, isopropyl ester The title compound was prepared in 40% (overall yield) as a white solid following a procedure analogous to that used to prepare spiro[cyclopropane-1,3'-[3H]indole]-2-carboxylic acid-1',2'-dihydro-2'-oxo-5'-bromo, ethyl ester. MS: m/z 264 [M+1]$^+$.

Example 16

Preparation of spiro[cyclopropane-1,3'-[3H]indole]-2-carboxylic acid-1',2'-dihydro-2'-oxo-5'-bromo, isopropyl ester The title compound was prepared in 38% (overall yield) as a white solid following a procedure analogous to that used to prepare spiro[cyclopropane-1,3'-[3H]indole]-2-carboxylic acid-1',2'-dihydro-2'-oxo-5'-bromo, ethyl ester. MS: m/z 324 [M+1]$^+$.

Example 17

Preparation of spiro[cyclopropane-1,3'-[3H]indole]-2-carboxylic acid-1',2'-dihydro-2'-oxo-ethyl ester The title compound was prepared in 45% (overall yield) as a white solid following a procedure analogous to that used to prepare spiro[cyclopropane-1,3'-[3H]indole]-2-carboxylic acid-1',2'-dihydro-2'-oxo-5'-bromo, ethyl ester. MS: m/z 232 [M+1]$^+$.

Example 18

Preparation of spiro[cyclopropane-1,3'-[3H]indole]-2-carboxylic acid-1',2'-dihydro-2'-oxo-5'-iodo, ethyl ester The title compound was prepared in 30% (overall yield) as a light yellow solid following a procedure analogous to that used to prepare spiro[cyclopropane-1,3'-[3H]indole]-2-carboxylic acid-1',2'-dihydro-2'-oxo-5'-bromo, ethyl ester. MS: m/z 357 [M+1]$^+$.

Example 19

Preparation of spiro[cyclopropane-1,3'-[3H]indole]-2-carboxylic acid-1',2'-dihydro-2'-oxo-5'-nitro, ethyl ester The title compound was prepared in 55% (overall yield) as a white solid following a procedure analogous to that used to prepare spiro[cyclopropane-1,3'-[3H]indole]-2-carboxylic acid, 1',2'-dihydro-2'-oxo-5'-bromo, ethyl ester. MS: m/z 277 [M+1]$^+$.

Example 20

Preparation of spiro[cyclopropane-1,3'-[3H]indole]-2-carboxylic acid-1',2'-dihydro-2'-oxo-5'-trifloromethoxy, ethyl ester The title compound was prepared in 52% (overall yield) as a white solid following a procedure analogous to that used to prepare spiro[cyclopropane-1,3'-[3H]indole]-2-carboxylic acid-1',2'-dihydro-2'-oxo-5'-bromo, ethyl ester. MS: m/z 316 [M+1]$^+$.

Example 21

Preparation of spiro[cyclopropane-1,3'-[3H]indole]-2-carboxylic acid-1',2'-dihydro-2'-oxo-5'-chloro-7'-methyl, ethyl ester The title compound was prepared in 45% (overall yield) as a white solid following a procedure analogous to that used to prepare spiro[cyclopropane-1,3'-[3H]indole]-2-carboxylic acid-1',2'-dihydro-2'-oxo-5'-bromo, ethyl ester. MS: m/z 280 [M+1]$^+$.

Example 22

Preparation of spiro[cyclopropane-1,3'-[3H]indole]-2-carboxylic acid-1',2'-dihydro-2'-oxo-5'-bromo-N-methoxy-N-methyl acetamide The title compound was prepared in 47% (overall yield) as a white solid following a procedure analogous to that used to prepare spiro[cyclopropane-1,3'-[3H]indole]-2-carboxylic acid, 1',2'-dihydro-2'-oxo-, 5'-bromo, ethyl ester. MS: m/z 325 [M+1]+.

Example 23

Preparation of spiro[cyclopropane-1,3'-[3H]indole]-2-carboxylic acid-1',2'-dihydro-2'-oxo-5'-bromo, tert-butyl ester The title compound was prepared in 58% (overall yield) as a white solid following a procedure analogous to that used to prepare spiro[cyclopropane-1,3'-[3H]indole]-2-carboxylic acid-1',2'-dihydro-2'-oxo-5'-bromo, ethyl ester. MS: m/z 338 [M+1]+.

Example 24

Preparation of spiro[cyclopropane-1,3'-[3H]indole]-2-carboxylic acid, 1',2'-dihydro-2'-oxo-5',7'-dimethyl, ethyl ester The title compound was prepared in 49% (overall yield) as a white solid following a procedure analogous to that used to prepare spiro[cyclopropane-1,3'-[3H]indole]-2-carboxylic acid-1',2'-dihydro-2'-oxo-5'-bromo, ethyl ester. MS: m/z 260 [M+1]+.

Example 25

Preparation of spiro[cyclopropane-1,3'-[3H]indole]-2-carboxylic acid-1',2'-dihydro-2'-oxo-6'-chloro, ethyl ester The title compound was prepared in 35% (overall yield) as a white solid following a procedure analogous to that used to prepare spiro[cyclopropane-1,3'-[3H]indole]-2-carboxylic acid-1',2'-dihydro-2'-oxo-5'-bromo, ethyl ester. MS: m/z 266 [M+1]+.

Example 26

Preparation of spiro[cyclopropane-1,3'-[3H]indole]-2-carboxylic acid-1',2'-dihydro-2'-oxo-5',6'-dichloro, ethyl ester The title compound was prepared in 49% (overall yield) as a white solid following a procedure analogous to that used to prepare spiro[cyclopropane-1,3'-[3H]indole]-2-carboxylic acid-1',2'-dihydro-2'-oxo-5'-bromo, ethyl ester. MS: m/z 300 [M+1]+.

Example 27

Preparation of spiro[cyclopropane-1,3'-[3H]indole]-2-carboxylic acid-1',2'-dihydro-2'-oxo-4'-bromo, ethyl ester The title compound was prepared in 35% (overall yield) as a white solid following a procedure analogous to that used to prepare spiro[cyclopropane-1,3'-[3H]indole]-2-carboxylic acid-1',2'-dihydro-2'-oxo-5'-bromo, ethyl ester. MS: m/z 311 [M+1]+.

Example 28

Preparation of spiro[cyclopropane-1,3'-[3H]indole]-2-carboxylic acid-1',2'-dihydro-2'-oxo-6'-bromo, ethyl ester The title compound was prepared in 35% (overall yield) as a white solid following a procedure analogous to that used to prepare spiro[cyclopropane-1,3'-[3H]indole]-2-carboxylic acid, 1',2'-dihydro-2'-oxo-, 5'-bromo, ethyl ester. MS: m/z 311 [M+1]+.

Example 29

Preparation of spiro[cyclopropane-1,3'-[3H]indole]-2-carboxylic acid-1',2'-dihydro-2'-oxo-5'-bromo, benzyl ester The title compound was prepared in 45% (overall yield) as a white solid following a procedure analogous to that used to prepare spiro[cyclopropane-1,3'-[3H]indole]-2-carboxylic acid, 1',2'-dihydro-2'-oxo-5'-bromo, ethyl ester. MS: m/z 372 [M+1]+.

Example 30

Preparation of spiro[cyclopropane-1,3'-[3H]indole]-2-carboxylic acid-1',2'-dihydro-2'-oxo-5'-bromo-3,3-diethyl, ethyl ester The title compound was prepared in 35% (overall yield) as a white solid following a procedure analogous to that used to prepare spiro[cyclopropane-1,3'-[3H]indole]-2-carboxylic acid-1',2'-dihydro-2'-oxo-5'-bromo-3,3-diethyl, ethyl ester. MS: m/z 366 [M+1]+.

Example 31

Preparation of spiro[cyclopropane-1,3'-[3H]indole]-2-carboxylic acid-1',2'-dihydro-2'-oxo-5'-bromo-3-ethyl, ethyl ester The title compound was prepared in 20% (overall yield) as a white solid following a procedure analogous to that used to prepare spiro[cyclopropane-1,3'-[3H]indole]-2-carboxylic acid-1',2'-dihydro-2'-oxo-5'-bromo-3,3-diethyl, ethyl ester. MS: m/z 338 [M+1]+.

Example 32

Preparation of spiro[cyclopropane-1,3'-[3H]indole]-2-carboxylic acid-1',2'-dihydro-2'-oxo-5'-[2"-thiophene], ethyl ester The title compound was prepared in 90% (overall yield) as a white solid following a procedure analogous to that used to prepare spiro[cyclopropane-1,3'-[3H]indole]-2-carboxylic acid-1',2'-dihydro-2'-oxo-5'-[2"-furfuryl], ethyl ester. MS: m/z 314 [M+1]$^+$.

Example 33

Preparation of spiro[cyclopropane-1,3'-[3H]indole]-2-carboxylic acid-1',2'-dihydro-2'-oxo-5'-phenyl, ethyl ester The title compound was prepared in 95% (overall yield) as a white solid following a procedure analogous to that used to prepare spiro[cyclopropane-1,3'-[3H]indole]-2-carboxylic acid-1',2'-dihydro-2'-oxo-5'-[2"-furfuryl], ethyl ester. MS: m/z 308 [M+1]$^+$.

Example 34

Preparation of 5'-chloro-2-(2-quinoline)-spiro[cyclopropane-1,3'-[3H]indol]-2'(1'H)-one The title compound was prepared in 55% (overall yield) as a white solid following a procedure analogous to that used to prepare 5'-chloro-2-(2-pyridinyl)-spiro[cyclopropane-1,3'-[3H]indol]-2'(1'H)-one. MS: m/z 321 [M+1]$^+$.

Example 35

Preparation of 5'-chloro-2-(3-thiophene)-spiro[cyclopropane-1,3'-[3H]indol]-2'(1'H)-one The title compound was prepared in 45% (overall yield) as a white solid following a procedure analogous to that used to prepare 5'-chloro-2-(2-pyridinyl)-spiro[cyclopropane-1,3'-[3H]indol]-2'(1'H)-one. MS: m/z 276 [M+1]$^+$.

Example 36

Preparation of 5'-chloro-2-(4,5-dimethyl-2-furfuryl)-spiro[cyclopropane-1,3'-[3H]indol]-2'(1'H)-one The title compound was prepared in 35% (overall yield) as a white solid following a procedure analogous to that used to prepare 5'-chloro-2-(2-pyridinyl)-spiro[cyclopropane-1,3'-[3H]indol]-2'(1'H)-one. MS: m/z 288 [M+1]$^+$.

Example 37

Preparation of 5'-chloro-2-(5-ethyl-2-furfuryl)-spiro[cyclopropane-1,3'-[3H]indol]-2'(1'H)-one The title compound was prepared in 30% (overall yield) as a white solid following a procedure analogous to that used to prepare 5'-chloro-2-(2-pyridinyl)-spiro[cyclopropane-1,3'-[3H]indol]-2'(1'H)-one. MS: m/z 288 [M+1]$^+$.

Example 38

Preparation of 5'-chloro-2-(5-methyl-2-furfuryl)-spiro[cyclopropane-1,3'-[3H]indol]-2'(1'H)-one The title compound was prepared in 39% (overall yield) as a white solid following a procedure analogous to that used to prepare 5'-chloro-2-(2-pyridinyl)-spiro[cyclopropane-1,3'-[3H]indol]-2'(1'H)-one. MS: m/z 274 [M+1]$^+$.

Example 39

Preparation of 5'-chloro-2-(4-fluorophenyl)-spiro[cyclopropane-1,3'-[3H]indol]-2'(1'H)-one The title compound was prepared in 45% (overall yield) as a white solid following a procedure analogous to that used to prepare 5'-chloro-2-(2-pyridinyl)-spiro[cyclopropane-1,3'-[3H]indol]-2'(1'H)-one. MS: m/z 288 [M+1]$^+$.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:
1. A compound having the formula:

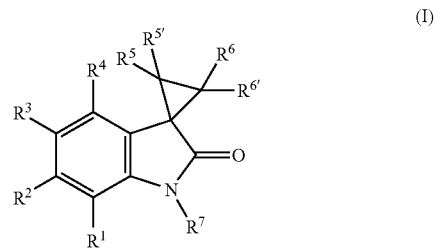

(I)

wherein $R^1$, $R^2$, $R^3$ and $R^4$ are members independently selected from H, substituted or unsubstituted alkyl, substituted or unsubstituted heteroalkyl, substituted or unsubstituted aryl, substituted or unsubstituted heteroaryl, $OR^8$, $NO_2$, CN and halogen;

wherein $R^8$ is a member selected from H and substituted or unsubstituted alkyl;

$R^5$ and $R^{5'}$ are members independently selected from substituted alkyl, substituted or unsubstituted alkenyl or alkynyl, substituted or unsubstituted cycloalkyl, substituted or unsubstituted heteroalkyl, substituted or unsubstituted aryl, substituted or unsubstituted heteroaryl, CN, $SR^9$ and $C(O)R^9$;

wherein $R^9$ is a member selected from H, substituted or unsubstituted alkyl, substituted or unsubstituted heteroalkyl, substituted or unsubstituted aryl, $NR^{10}R^{11}$ and $OR^{11}$;

wherein $R^{10}$ is a member selected from H, substituted or unsubstituted alkyl, and $OR^{12}$;

wherein $R^{12}$ is a member selected from H, substituted or unsubstituted alkyl, and substituted or unsubstituted heteroalkyl;

$R^{11}$ is a member selected from H, $C(O)R^{13}$, substituted or unsubstituted alkyl, substituted or unsubstituted heteroalkyl, substituted or unsubstituted aryl, and substituted or unsubstituted heterocycloalkyl, and wherein $R^{10}$ and $R^{11}$, together with the nitrogen to which they are bound, are optionally joined to form a substituted or unsubstituted heterocycloalkyl ring system having from 3 to 7 members;

wherein $R^{13}$ is a member selected from H, substituted or unsubstituted alkyl, substituted or unsubstituted heteroalkyl, and $NR^{14}R^{15}$;

wherein $R^{14}$ and $R^{15}$ are members independently selected from H, substituted or unsubstituted alkyl, and substituted or unsubstituted heteroalkyl;

$R^6$ and $R^{6'}$ are members independently selected from H, substituted or unsubstituted alkyl, and $C(O)R^{16}$;

wherein $R^{16}$ is a member selected from substituted or unsubstituted alkyl, substituted or unsubstituted heteroalkyl, $NR^{17}R^{18}$ and $OR^{17}$;

wherein $R^{17}$ and $R^{18}$ are members independently selected from H, substituted or unsubstituted alkyl, substituted or unsubstituted heteroalkyl, and substituted or unsubstituted aryl; and $R^7$ is a member selected from H, substituted or unsubstituted alkyl, and substituted or unsubstituted heteroalkyl.

2. The compound according to claim 1, wherein at least one of $R^5$ and $R^{5'}$ is a member selected from substituted or unsubstituted phenyl, substituted or unsubstituted pyridyl, substituted or unsubstituted furanyl, substituted or unsubstituted benzofuranyl, substituted or unsubstituted quinolinyl, and substituted or unsubstituted thienyl.

3. The compound according to claim 1, wherein at least one of $R^{10}$ and $R^{11}$ is substituted or unsubstituted $C_1$–$C_6$ alkyl.

4. The compound according to claim 1, wherein at least one of $R^6$ and $R^{6'}$ is a member selected from substituted or unsubstituted $C_1$–$C_6$ alkyl.

5. The compound according to claim 1, having the formula:

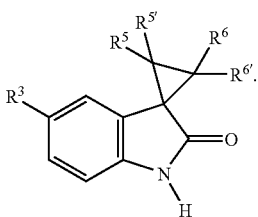

6. The compound according to claim 5, having the formula:

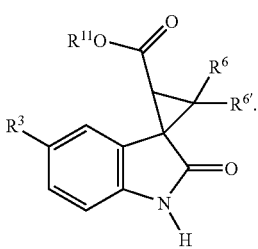

7. The compound according to claim 6, wherein $R^{11}$ is substituted or unsubstituted $C_1$–$C_6$ alkyl.

8. The compound according to claim 5, wherein at least one of $R^5$ and $R^{5'}$ is a member selected from substituted or unsubstituted:

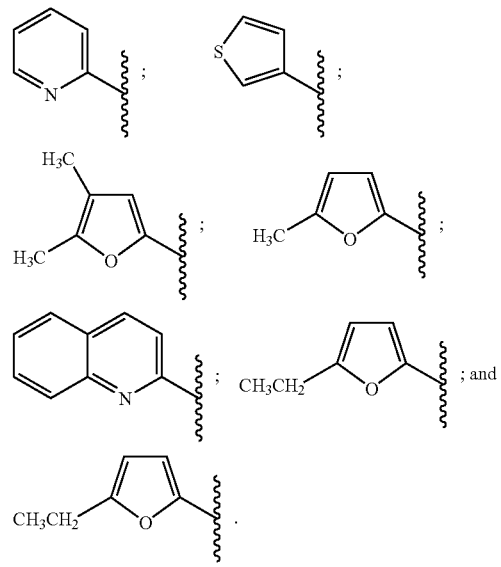

9. The compound according to claim 5, wherein $R^6$ $R^{6'}$ are independently selected from substituted or unsubstituted methyl and substituted or unsubstituted ethyl.

10. A pharmaceutical formulation comprising a compound according to claim 1 and a pharmaceutically acceptable carrier.

11. A method of inhibiting HIV in a cell, said method comprising contacting said cell with an amount of a compound according to claim 1 sufficient to inhibit said HIV.

12. A method of inhibiting reverse transcriptase in a cell, said method comprising contacting said cell with an amount of a compound according to claim 1 sufficient to inhibit said reverse transcriptase.

13. The method according to claim 11, wherein said cell is in a human.

14. The method according to claim 12, wherein said cell is in a human.

15. A method of treating HIV infection in a human subject comprising administering to said subject an amount of a compound according to claim 1, sufficient to treat said HIV infection.

16. The method according to claim 15, wherein said HIV is a drug resistant mutant.

17. The compound of claim 1, wherein said compound is selected from the group consisting of

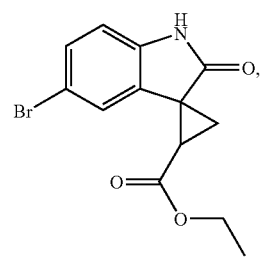

-continued
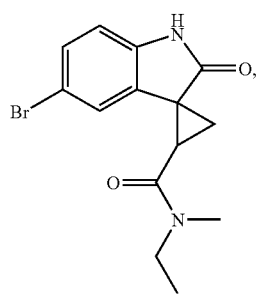
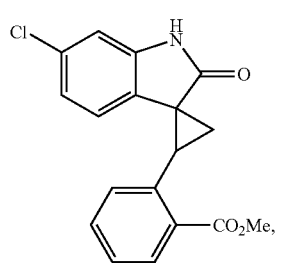
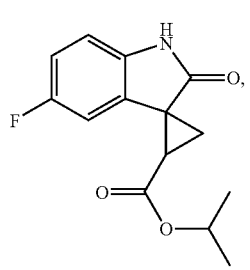
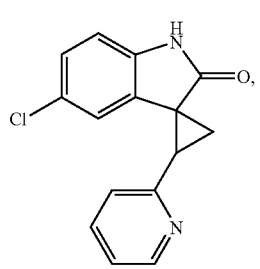
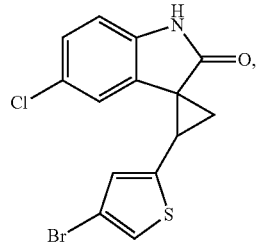
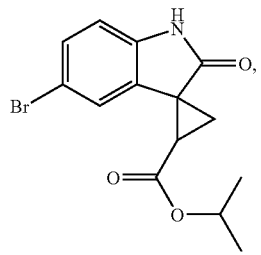
-continued
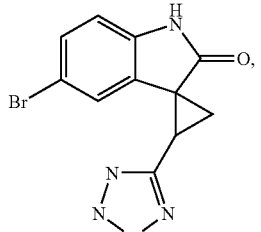
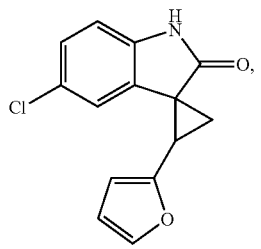
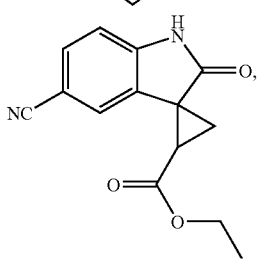
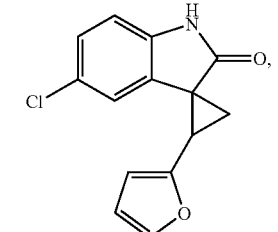
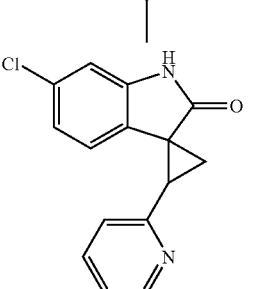
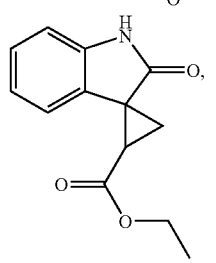

-continued
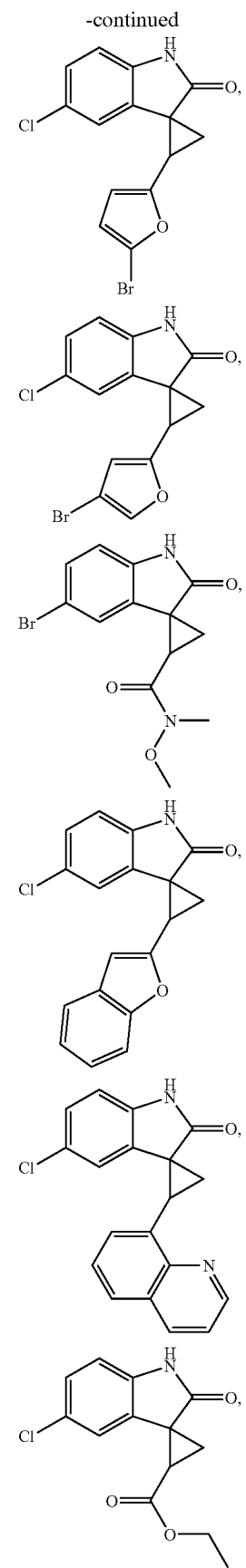
-continued
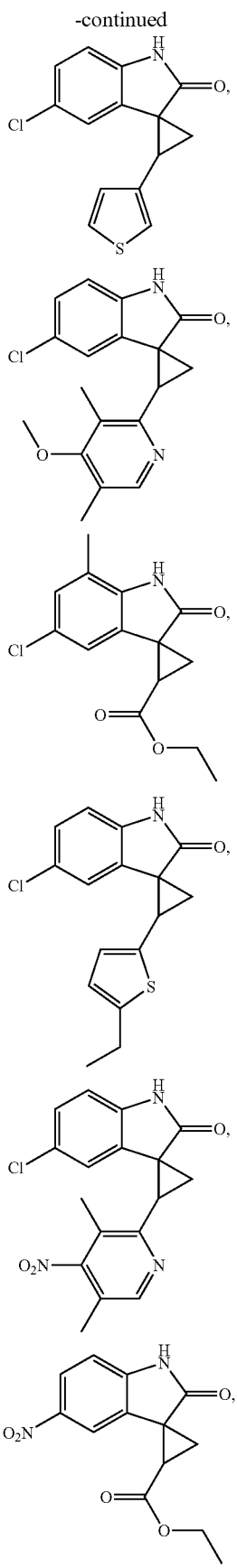

-continued
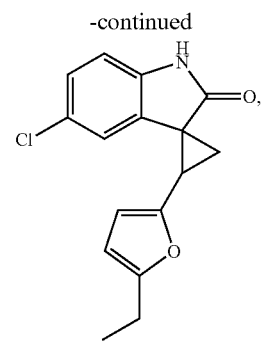
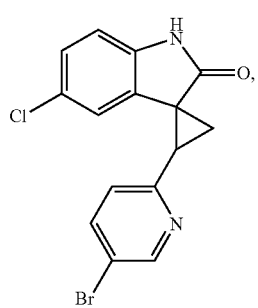
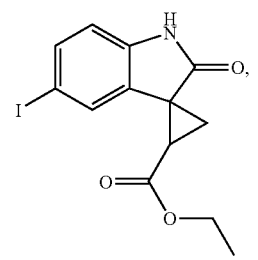
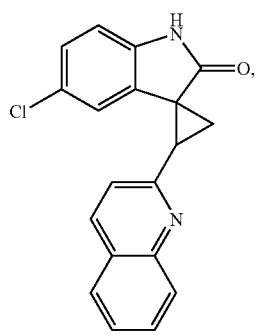
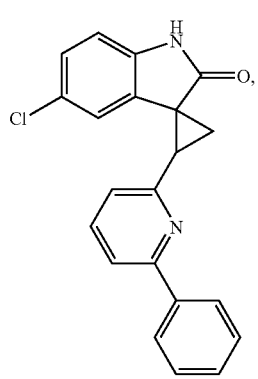
-continued
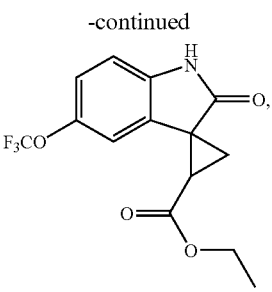
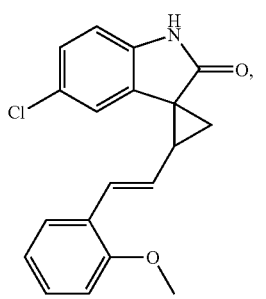
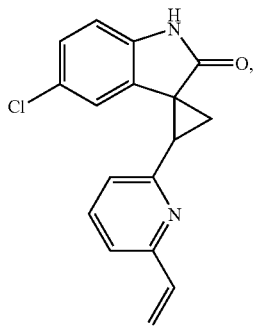
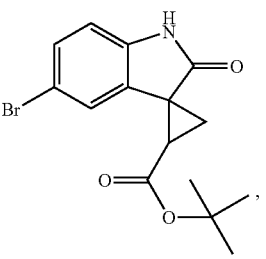
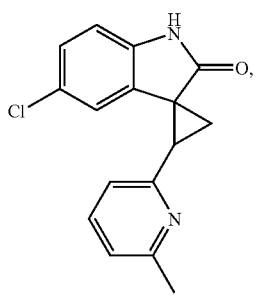

-continued
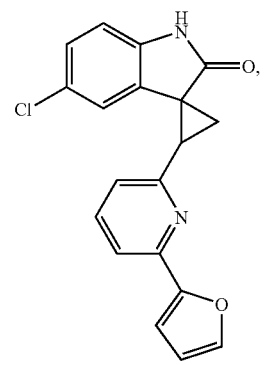
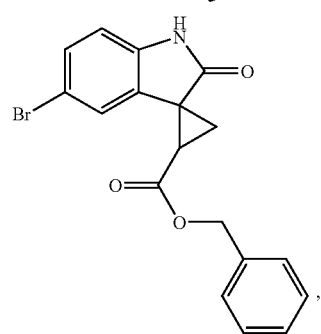
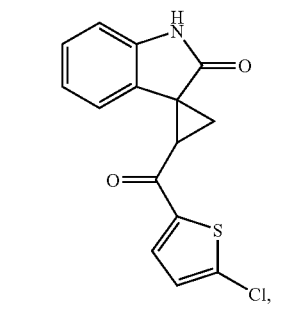
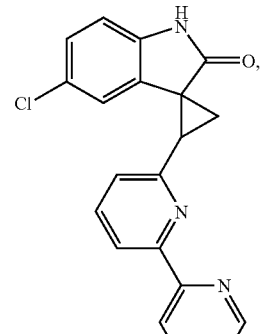
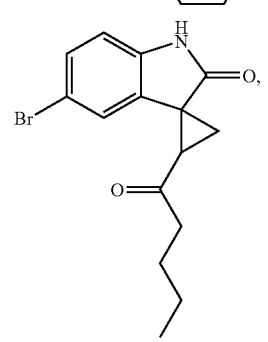
-continued
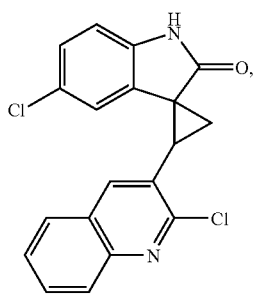
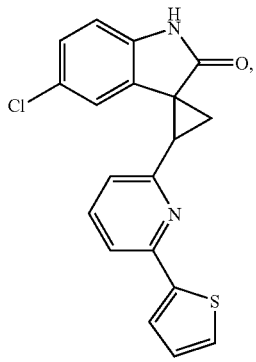
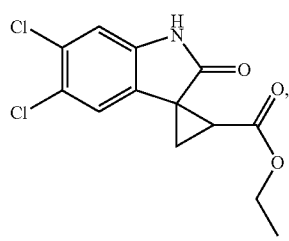
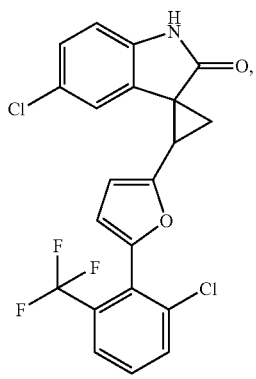
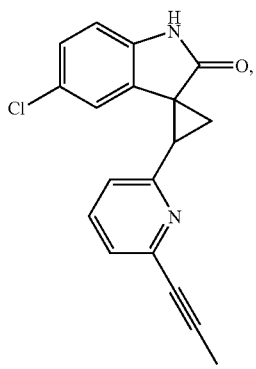

-continued
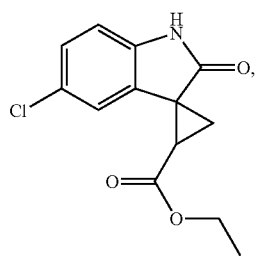
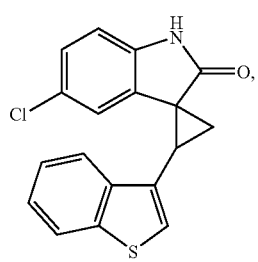
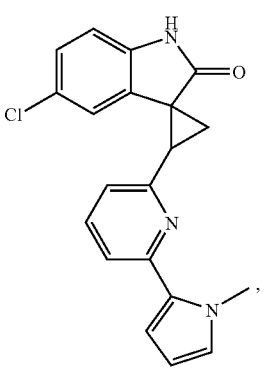
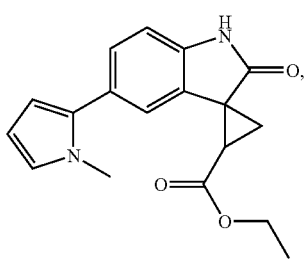
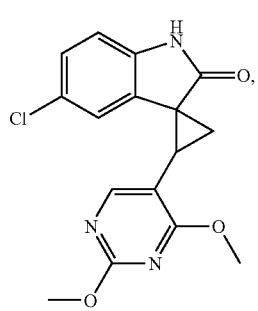
-continued
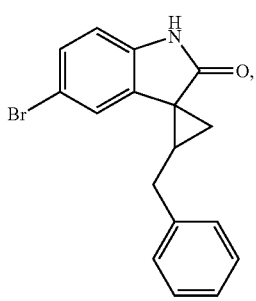
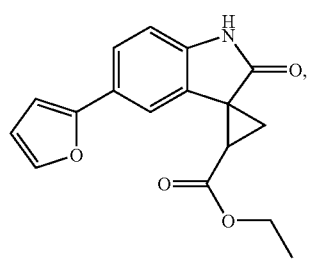
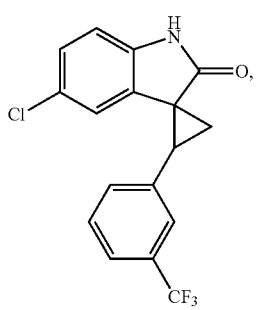
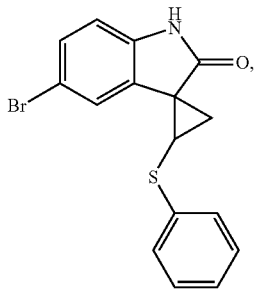
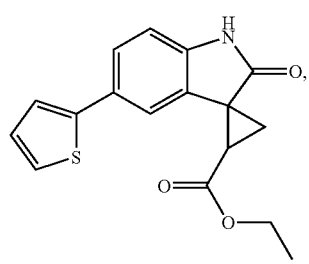

-continued
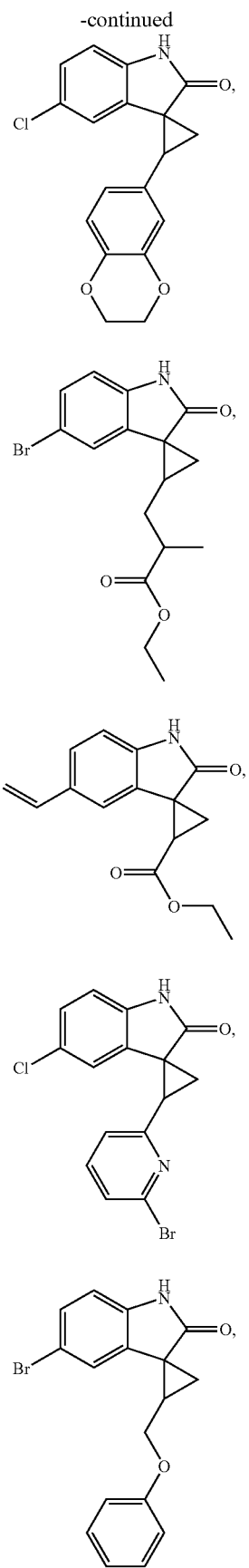
-continued
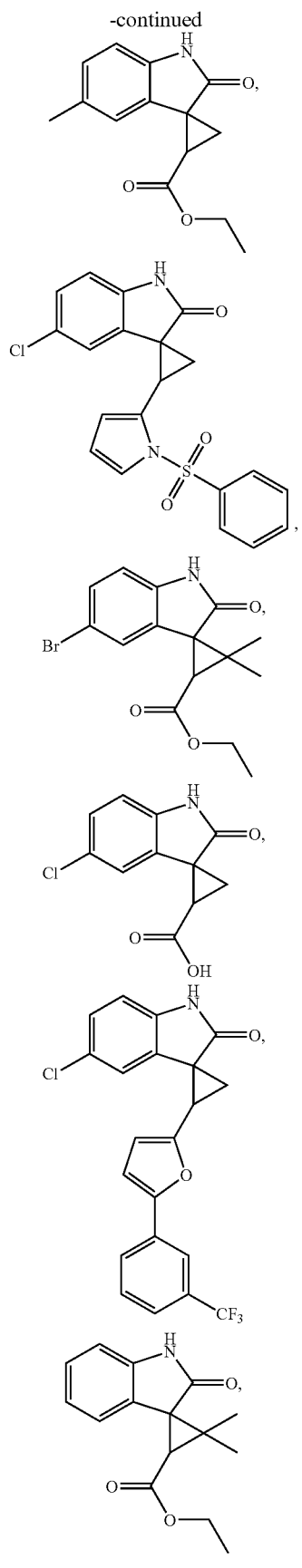

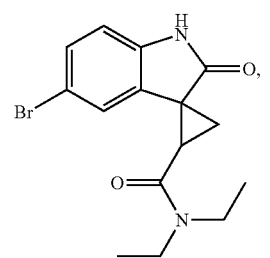
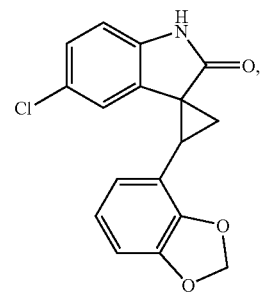
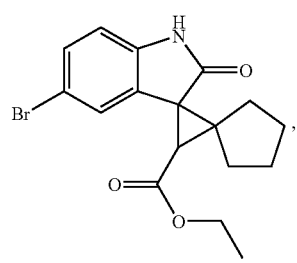
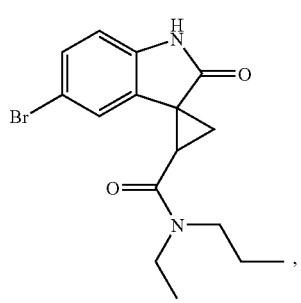
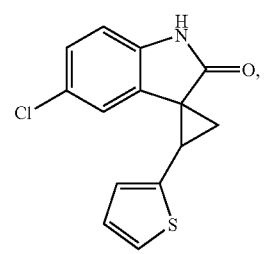
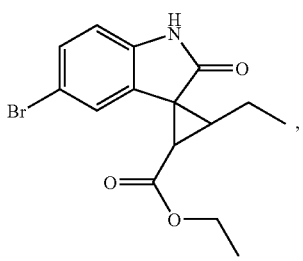
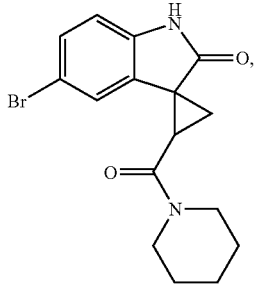
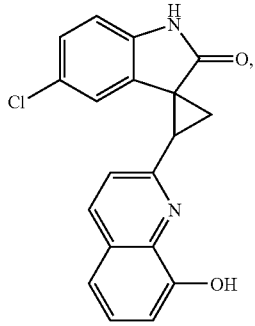
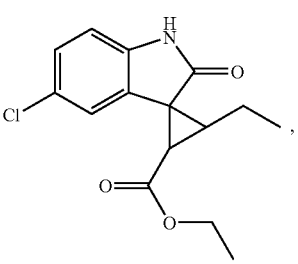
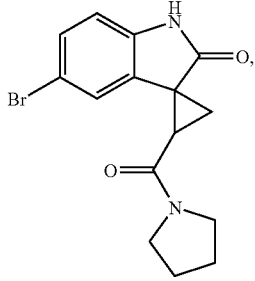
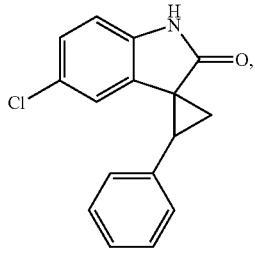

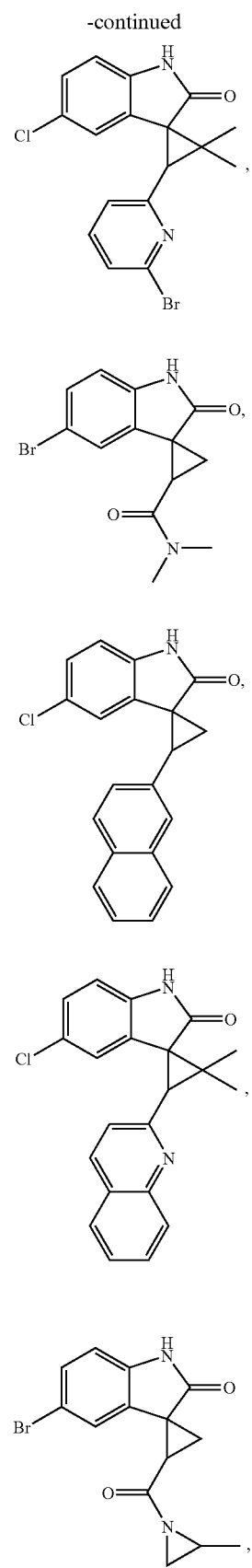
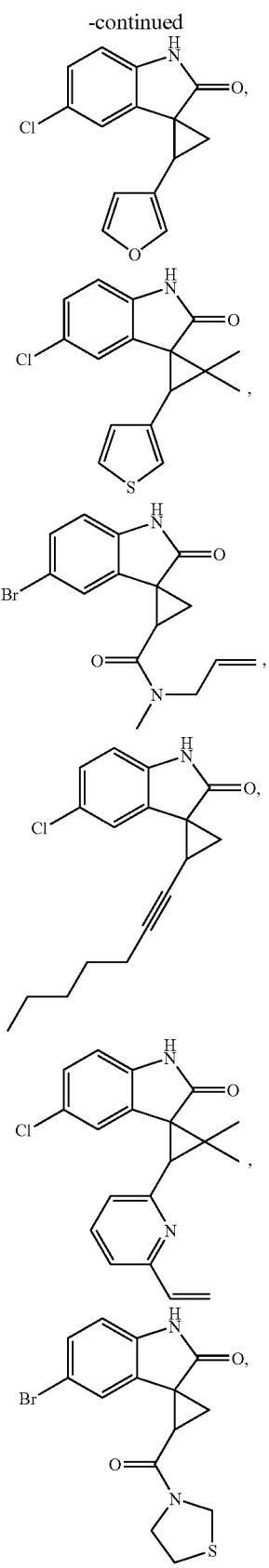

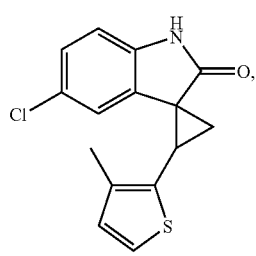

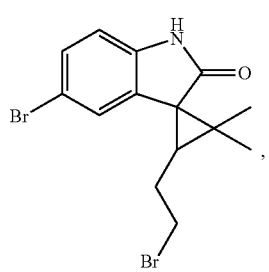

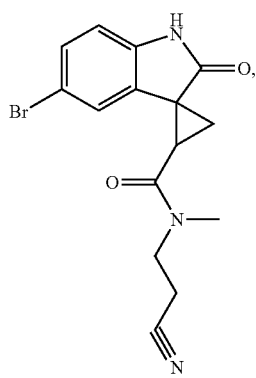

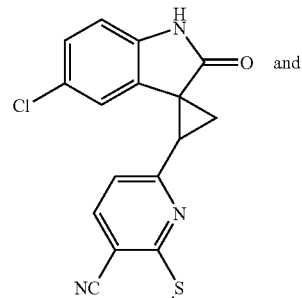

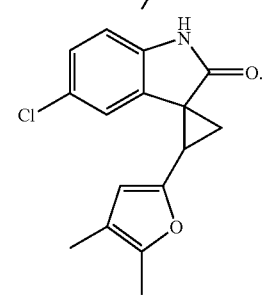

18. A pharmaceutical formulation comprising a compound according to claim 17 and a pharmaceutically acceptable carrier.

19. A method of inhibiting HIV in a cell, said method comprising contacting said cell with an amount of a compound according to claim 17 sufficient to inhibit said HIV.

20. A method of inhibiting reverse transcriptase in a cell, said method comprising contacting said cell with an amount of a compound according to claim 17 sufficient to inhibit said reverse transcriptase.

21. The method according to claim 19, wherein said cell is in a human.

22. The method according to claim 20, wherein said cell is in a human.

23. A method of treating HIV infection in a human subject comprising administering to said subject an amount of a compound according to claim 17, sufficient to treat said HIV infection.

24. The method according to claim 23, wherein said HIV is a drug resistant mutant.

* * * * *